United States Patent
Lewis et al.

(10) Patent No.: US 10,189,871 B2
(45) Date of Patent: Jan. 29, 2019

(54) TRANSITION METAL COMPLEXES FOR ENANTIOSELECTIVE CATALYSIS OF CARBON-CARBON, CARBON-HETEROATOM, AND CARBON-HYDROGEN BOND FORMING REACTIONS

(71) Applicants: Kyle G. Lewis, Houston, TX (US); John A. Gladysz, College Station, TX (US); Subrata K. Ghosh, College Station, TX (US)

(72) Inventors: Kyle G. Lewis, Houston, TX (US); John A. Gladysz, College Station, TX (US); Subrata K. Ghosh, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 78 days.

(21) Appl. No.: 15/243,054

(22) Filed: Aug. 22, 2016

(65) Prior Publication Data
US 2017/0044198 A1 Feb. 16, 2017

Related U.S. Application Data

(62) Division of application No. 14/417,655, filed as application No. PCT/US2013/052569 on Jul. 29, 2013, now Pat. No. 9,446,393.

(60) Provisional application No. 61/676,683, filed on Jul. 27, 2012.

(51) Int. Cl.
| | | |
|---|---|---|
| C07F 15/06 | (2006.01) | |
| C07B 53/00 | (2006.01) | |
| C07C 211/65 | (2006.01) | |
| B01J 31/02 | (2006.01) | |
| B01J 31/14 | (2006.01) | |
| B01J 31/18 | (2006.01) | |
| B01J 31/22 | (2006.01) | |
| C07F 5/02 | (2006.01) | |

(52) U.S. Cl.
CPC ......... *C07F 15/065* (2013.01); *B01J 31/0255* (2013.01); *B01J 31/146* (2013.01); *B01J 31/1805* (2013.01); *B01J 31/22* (2013.01); *B01J 31/2295* (2013.01); *C07B 53/00* (2013.01); *C07C 211/65* (2013.01); *C07F 5/027* (2013.01); *B01J 2231/32* (2013.01); *B01J 2231/323* (2013.01); *B01J 2231/341* (2013.01); *B01J 2531/845* (2013.01)

(58) Field of Classification Search
CPC ........ C07F 15/065; C07F 5/027; B01J 31/146
See application file for complete search history.

(56) References Cited

U.S. PATENT DOCUMENTS

| | | |
|---|---|---|
| 4,182,814 A | 1/1980 | Bernemann et al. |
| 4,472,559 A | 9/1984 | Maehara et al. |
| 4,598,091 A | 7/1986 | Schonenberger et al. |
| 5,663,393 A | 9/1997 | Jacobsen et al. |
| 6,410,749 B1 | 6/2002 | Katayama et al. |
| 6,686,505 B2 | 2/2004 | Watanabe et al. |

OTHER PUBLICATIONS

Nagababu (Bioragnic Chemistry and Applications; 2007, pp. 1-8).*
Bosnich, et al., "A Regional Rule for the Optical Activity of Conformational Isomers of Octahedral Transition Metal Complexes", J. Am. Chem. Soc., 94 (10), pp. 3425-3437, May 17, 1972.
International Search Report and Written Opinion for PCT/US13/52569, dated Feb. 19, 2014.
International Preliminary Report on Patentability for PCT/US2013/052569, dated Feb. 5, 2015.
Pozzi et al., "Fluorous chiral ligands for novel catalytic systems" Coordination Chemistry Reviews, vol. 242, Issues 1-2, pp. 115-124, Jul. 2003.
Nagababu, et al., "DNA Binding and Photocleavage Studies of Cobalt (III) Ethylenediamine Pyridine Complexes: [Co(en)2(py)2]3+ and [Co(en)2(mepy)2]3+", Metal-Based Drugs, vol. 2008, pp. 1-8 (2008).
Nagababu, et al., "DNA Binding and Photocleavage Studies of Cobalt(III) Polypyridine Complexes: [Co(en)2PIP]3+, [Co(en)2IP]3+, and [Co(en)2phen-dione]3+", Bioinorganic Chemistry and Applications, vol. 2007, pp. 1-8 (2007).
Summers et al., "Observation of distinct cadmium-113 NMR signals for complexes of nitrogen-donor chelate ligands in solution at ambient temperature" Inorg. Chem., 23 (5), pp. 521-523, Feb. 1984.
Woldbye, et al., "The Effect of Ring Size and Conformation on the Rotatory Strength of tris-(Bidentate) Complexes", Proc. R. Soc. Land. A, 297 (1967), Feb. 27, 1967.
Perera, et al., "Several novel N-donor tridentate ligands formed in chemical studies of new fac-Re(CO)3 complexes relevant to fac-99mTc(CO)3 radiopharmaceuticals: attack of a terminal amine on coordinated acetonitrile." Inorg. Chern., 49 (5), pp. 2123-2131 (2010).
Del Piero, et al., "Solvent role on cobalt(II) dioxygen carriers based on simple polyamine ligands", Helvetica Chimica Acta, vol. 88, Issue 4, Article first published online: Apr. 19, 2005.

(Continued)

*Primary Examiner* — Pancham Bakshi
(74) *Attorney, Agent, or Firm* — Winstead PC

(57) ABSTRACT

In some embodiments, the present disclosure pertains to a compound, comprising a transition metal complex having the formula $\Phi\text{-}[M\,(x,y)\text{-}L_1\,(w,v)\text{-}L_2\,(t,u)\text{-}L_3]^{p+}An^-{}_m Z^-{}_{p-m}$. In an embodiment of the present disclosure $\Phi$ may be $\Lambda$. In another embodiment $\Phi$ may be $\Delta$. In some embodiments of the present disclosure, M is a transition metal. In a related embodiment, p is an integer corresponding to the oxidation state of M. In some embodiments of the present disclosure, each of x, y, w, v, t, and u independently comprise R. In other embodiments, each of x, y, w, v, t, and u independently comprise S. In an embodiment of the present disclosure, each of $L_1$, $L_2$, and $L_3$ independently is a ligand comprising a substituted diamine. In some embodiments, An⁻ comprises a lipophilic anion, where m is from 1 to 3, and where Z⁻ comprises an optional second anion.

5 Claims, 25 Drawing Sheets

(56) References Cited

OTHER PUBLICATIONS

Jorge et al., "On the Origin of the Optical Activity in Tris-diamine Complexes of Co(III) and Rh(III): A Simple Model Based on Time-Dependent Density Function Theory", J. Am. Chem. Soc. 2005, 127, 975-985 (2005).

Jorge et al., "On the Origin of the Optical Activity in the d-d Transition Region of Tris-Bidentate Co(III) and Rh(III) Complexes", Inorg. Chem., 42 (26), pp. 8902-8910 (2003).

Judkins et al., Optical rotatory strength of tris-bidentate cobalt (III) complexes, Inorg. Chem., 13(4), pp. 945-950 (1974).

* cited by examiner n=2,3,4
X=1,2,3

(S) CONFIGURATION     (R) CONFIGURATION

Λ-[Co(en)₂(R)-enCH₂CH₂CH₂NMe₂]³⁺    Δ-[Co(en)₂(R)-enCH₂CH₂CH₂NMe₂]³⁺

[Co(en)2(S)-enCH$_2$CH$_2$CH$_2$NMe$_2$H]$^{4+}$4Cl-

Λ

FRACTION 2

Λ-[Co(en)₂(S)-enCH₂CH₂CH₂NMe₂]³⁺ 3BAr_f⁻

Δ-[Co(en)₂(S)-enCH₂CH₂CH₂NMe₂]³⁺ 3BAr_f⁻

FRACTION 1

FRACTION 2

[Fr 1] 3BArf− ethylenediamine cyclohexanediamine
(R,R), (S,S), (S,R)

diphenylethylenediamine
(R,R), (S,S), (S,R)

2,2'-bypyridine n=1,2,3,4,5 n=0,1,2,3,4,5...

TRANSITION METAL COMPLEXES FOR ENANTIOSELECTIVE CATALYSIS OF CARBON-CARBON, CARBON-HETEROATOM, AND CARBON-HYDROGEN BOND FORMING REACTIONS

CROSS-REFERENCE TO RELATED APPLICATIONS

This application is a divisional application of U.S. patent application Ser. No. 14/417,655, filed on Jul. 29, 2013. This application claims priority to U.S. Provisional Application No. 61/676,683, filed Jul. 27, 2012. The entirety of the aforementioned applications is incorporated herein by reference.

FIELD

This invention relates to transition metal/substituted organo di-amine ligand complexes and their function as catalysts, particularly for carbon-carbon, carbon-heteroatom, and carbon-hydrogen bond forming reactions.

BACKGROUND

Enantioselective catalysts are desirable for producing high value added enantiopure chemicals. Examples of applications of enantiopure chemicals are as pharmaceutical chemicals and as agricultural chemicals. Production of pharmaceutical chemicals or that of agricultural chemicals tends to involve carbon-carbon, carbon-heteroatom, and/or carbon-hydrogen bond forming reactions. Enantiopure chemicals may be alternately described as optically active, or as right or left rotation forms, or as chiral. Enantiopure chemicals possess the characteristic that they have a 3 dimensional handedness and are substantially pure. In addition, enantiopure chemicals can be at least one of the other of two forms that are not mirror images of each other.

The use of existing transition metal complexes as catalysts, for mediating carbon-carbon, carbon-heteroatom, and carbon-hydrogen bond forming reaction, is limited for commercial applications. The limited commercial use is attributed to the existing transition metal complexes being substitution labile, having poor solubility in organic solvents, or further having low enantioselectivity. Therefore, there remains a need for substitution inert transition metal complexes with activity as enantioselective catalysts for carbon-carbon, carbon-heteroatom, and carbon-hydrogen bond forming reactions that are suitable for commercial/industrial applications.

SUMMARY

In some embodiments, the present disclosure pertains to a compound, comprising a transition metal complex having the formula $\Phi\text{-}[M\ (x,y)\text{-}L_1\ (w,v)\text{-}L_2\ (t,u)\text{-}L_3]^{p+}An^-_m Z^-_{p-m}$. In an embodiment of the present disclosure $\Phi$ may be $\Lambda$. In another embodiment $\Phi$ may be $\Delta$. In some embodiments of the present disclosure, M is a transition metal. In some embodiments, p is an integer corresponding to the oxidation state of M. In some embodiments of the present disclosure, each of x, y, w, v, t, and u independently comprise R. In other embodiments, each of x, y, w, v, t, and u independently comprise S. In some embodiments of the present disclosure, each of $L_1$, $L_2$, and $L_3$ independently is a ligand comprising a substituted diamine. In some embodiments $An^-$ comprises a lipophilic anion, where m is from 1 to 3, and where $Z^-$ comprises an optional second anion.

In some embodiments, the present disclosure relates to a compound comprising a transition metal complex having the formula $\Phi\text{-}[M\ ((x,y)\text{-}L_1)_{3-b-c}\ ((w,v)\text{-}L_2)_b((t,u)\text{-}L_3)_c]^{p+}An^-_m Z^-_{p-m}$. In some embodiments of the present disclosure, $\Phi$ is $\Lambda$. In some embodiments of the present disclosure, $\Phi$ is $\Delta$. In some embodiments of the present disclosure, M is a transition metal. In some embodiments, p is an integer corresponding to the oxidation state of M. In some embodiments, each of x, y, w, v, t, and u independently comprises R. In other embodiments, each of x, y, w, v, t, and u independently comprises S. In some embodiments, each of $L_1$, $L_2$ and $L_3$ independently is a ligand comprising ethylene diamine. In some embodiments, $L_3$ is a ligand comprising a pendant Lewis base derivative of ethylene diamine. In some embodiments, c is from 1 to 3. In some embodiments, b is from 0 to 2. In some embodiments of the present disclosure, $An^-$ comprises a lipophilic anion, where m is from 1 to 3, and where $Z^-$ comprises a second anion.

In some embodiments, the present disclosure relates to a compound comprising a transition metal complex having the formula $\Phi\text{-}[M\ (x,y)\text{-}L_1\ (w,v)\text{-}L_2 XY]^{(p+a)+}An^-_m Z^-_{p-m}$. In some embodiments, $\Phi$ is $\Lambda$. In some embodiments, $\Phi$ is $\Delta$. In some embodiments of the present disclosure, M is a transition metal. In some embodiments, p is an integer corresponding to the oxidation state of M. In some embodiments, each of x, y, w, and v is independently R. In other embodiments, each of x, y, w, and v is independently S. In some embodiments of the present disclosure, each of $L_1$ and $L_2$ comprises a chelating ligand comprising at least two nitrogens. In some embodiments, each of $L_1$ and $L_2$ independently comprises a chelating ligand comprising at least two metal coordinating atoms. In some embodiments of the present disclosure, Y comprises a mono-coordinated diamine ligand. In some embodiments of the present disclosure, X comprises one out of a second mono-coordinated diamine ligand and a nucleophilic ligand. In some embodiments, "a" is the total charge of the mono-coordinated ligand(s). In some embodiments of the present disclosure, $An^-$ comprises a lipophilic anion, where m is from 1 to p, and where $Z^-$ comprises a second optional anion.

BRIEF DESCRIPTION OF THE DRAWINGS

FIG. 5A illustrates forming an intermediate cobalt complex with conventional anions forming a precursor cobalt salt, where the anion of the intermediate cobalt complex is the same as the anion of the precursor cobalt, and FIG. 5B illustrates forming a cobalt complex soluble in organic solvent by replacing at least one conventional anions with a lipophilic anion;

FIG. 6A illustrates use of the catalyst obtained by procedure 1 described herein and FIG. 6B illustrates use of the catalyst obtained by procedure 1b described herein;

DETAILED DESCRIPTION

Figure 1:
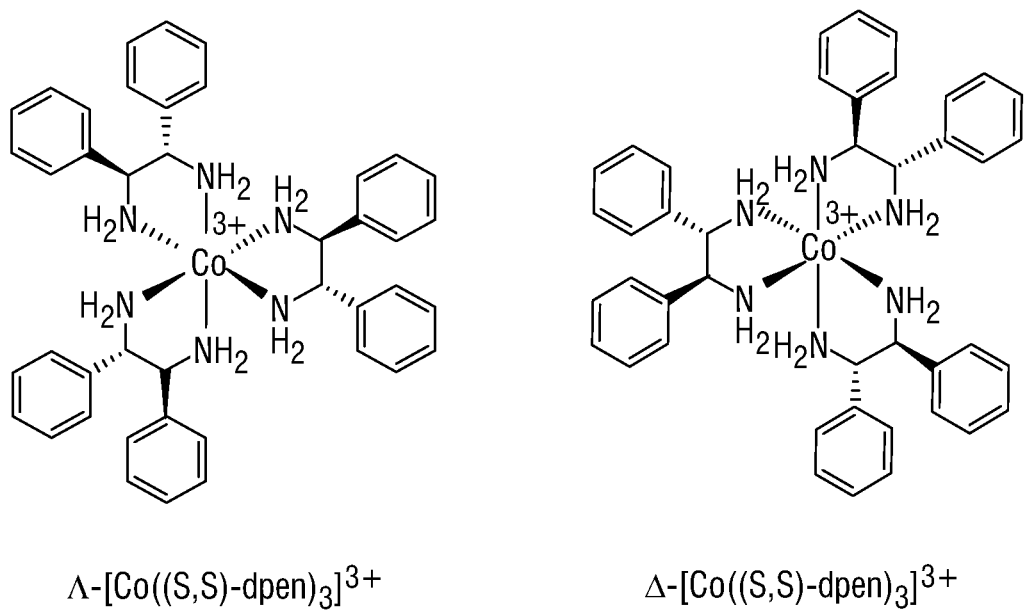
FIG. 1 depicts the two chiral configurations that center at the metal, $\Lambda$ and $\Delta$, illustrated with 3(S,S)-diphenylethylenediamine (DPEN) ligands and cobalt (Co) metal, $\Lambda$-[Co((S,S)-dpen)3]$^{3+}$ and $\Delta$-[Co((S,S)-dpen)3]$^{3+}$ respectively.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Described in U.S. Pat. No. 4,598,091 are (1,2)-diphenyl-ethylenediamine-platinum (II) complex compounds with antitumor activity. The compounds described have one (1,2)-diphenyl-ethylenediamine portion that may be optically active and two of an X ligand that is a physiologically compatible anion. The Pt(II) compounds described tend to be substitution labile. Substitution labile ligands tend to go on and off a metal center easily.

Described in U.S. Pat. No. 6,410,749 is a process for the preparation of optically active amino alcohols from corresponding α-aminocarbonyl compounds in the presence of an optically active transition metal complex. The transition metal complexes described tend to be soluble in organic solvents and to be substitution labile. Substitution lability in a catalyst tends to open up a binding site available for reactions.

Werner complexes were introduced by Werner in 1911. Werner salts of the chiral tris(ethylenediamine)-substituted octahedral cation $[Co(en)_3]^{3+}$ and related species have played important historical roles in the development of inorganic chemistry and stereochemistry. However, the known salts of $[Co(en)_3]^{3+}$ such as $[Co(en)_3]^{3+}(Cl^-)_3$, have been generally regarded as undesirable for catalysis because a) they are soluble only in water, whereas most industrial processes occur in organic solvents; and b) they are substitution inert, in that the complexes contained ligands that did not go on and off the metal center easily, to open up a binding site for reactions.

Described in Chem. Euro. J. 2008, 14, 5397-5400, by C. Ganzmann and J. Gladysz, is phase transfer of enantiopure Werner cations into organic solvents: an overlooked family of chiral hydrogen bond donors for enantioselective catalysis. This reference described $\Delta$-$[Co(en)3]^{3+}(Cl^-)_2$ $(BAr_f^-)_3 \cdot 14H_2O$ where $BAr_f^-$ is tetrakis[(3,5-trifluromethyl)phenyl]borate. This complex was reported to be soluble in $CH_2Cl_2$, acetone, ethyl acetate, THF, DMSO, and alcohols. The NH bonds of the complex were thought to be catalytic sites. However, the reported enantioselectivity was 33%, which tends to be insufficient for commercial applications. The work is further described in a master's thesis of Carola Ganzmann, reporting similarly low enantioselectivity. A need in the art exists for substitution inert metal complexes that can function as enantioselective catalysts for producing high value added enantiopure chemicals for commercial use.

The present disclosure relates to transition metal/substituted organo di-amine ligand complexes and their function as catalysts, particularly for carbon-carbon, carbon-heteroatom, and carbon-hydrogen bond forming reactions. More particularly, the present disclosure, in some embodiments relates to such complexes incorporating cobalt (Co), iron (Fe), nickel (Ni), chromium (Cr), manganese (Mn), molybdenum (Mo), tungsten (W), rhenium (Re), ruthenium (Ru), technetium (Tc), osmium (Os), rhodium (Rh), iridium (Jr), platinum (Pt), or palladium (Pd). In some embodiments, the present disclosure pertains to such complexes incorporating cobalt, iron, or nickel. Specifically, in some embodiments, the present disclosure relates to such complexes incorporating cobalt.

The transition metal complexes disclosed herein present a new class of complexes soluble in organic solvents and suitable as catalysts for enantioselective organic synthesis. The present inventors have discovered identities and arrangements of ligands that provide sufficient enantioselectivity to the transition metal complexes for commercial application as catalysts for the manufacture of enantiopure chemicals. As used herein, enantioselectivity may be expressed as enantiomeric excess. According to some embodiments, the transition metal complex has activity in enantioselective hydrogen bond mediating catalysis. According to some embodiments, the hydrogen bond mediating catalysis is suitable for carbon-carbon bond forming reactions. In some embodiments, the hydrogen bond mediating catalysis is suitable for carbon-heteroatom bond forming reactions. Alternatively or in combination, according to some embodiments, the hydrogen bond mediating catalysis is suitable for carbon-hydrogen bond forming reactions. The present metal complexes have the advantage of at least 60% entantioselectivity. For example, enatioselectivities of at least 75% have been achieved. More particularly, enantioselectivities of at least 85% have been achieved. Still more particularly, enantioselectivities of at least 94% have been achieved. The transition metal complexes disclosed herein further have the advantage of producing high yields. For example, conversions of at least 95% have been achieved. More particularly, conversions of at least 97% have been achieved. Still more particularly, conversions of at least 99% have been achieved.

According to some embodiments, transition metal complexes of type 1 are represented by the formula $\Phi$-[M (x,y)-$L_1$ (w,v)-$L_2$ (t,u)-$L_3]^{p+}An^-_m Z^-_{p-m}$, where $\Phi$ is $\Lambda$ or $\Delta$, where M is a transition metal, where p corresponds to the oxidation state of M, where each of x, y, w, v, t, and u is independently R or S, where each of $L_1$, $L_2$, and, $L_3$ independently represents a ligand that is a substituted diamine, where $An^-$ represents a lipophilic anion, m is from 1 to 3, and where $Z^-$ represents a conventional anion. Suitable substituted diamines include, but are not limited to, diphenylethylenediamine, derivatives of diphenylethylenediamine, and cyclohexanediamine.

According to some embodiments, transition metal complexes of type 2 are represented by the formula $\Phi$-[M $((x,y)-L_1)_{3-b-c}((w,v)-L_2)_b((t,u)-L_3)_c]^{p+}An^-_m Z^-_{p-m}$, where $\Phi$ is $\Lambda$ or $\Delta$, M is a transition metal, p corresponds to the oxidation state of M, where each of x, y, w, v, t, and u is independently R or S, where each of $L_1$ and $L_2$ independently represents a ligand that is ethylene diamine (also herein termed "EN" or alternately diaminoethane), where $L_3$ represents a ligand that comprises a pendant Lewis base derivative of EN, where c is from 1 to 3, where b is from 0 to 2, where $An^-$ represents a lipophilic anion, where m is from 1 to 3, and where $Z^-$ represents a conventional anion. Suitable ligands comprising a pendant Lewis base derivative of EN include, but are not limited to, $EN(CH_2)_n NR_1R_2$, where n is from 2 to 4. According to some embodiments, the pendant Lewis base derivative imparts biofunctionality to the transition metal complex, when the transition metal complex is used as a catalyst.

According to some embodiments, transition metal complexes of type 3 are represented by the formula $\Phi$-[M (x,y)-$L_1$ (w,v)-$L_2XY]^{(p+a)+}An^-_m Z^-_{p-m}$, where $\Phi$ is $\Lambda$ or $\Delta$, wherein M is a transition metal, where p is an integer corresponding to the oxidation state of M, where each of x, y, w, and v is independently R or S, wherein each of $L_1$, and $L_2$ comprises a chelating ligand comprising at least two nitrogens, where p is an integer corresponding to the oxidation state of M, wherein each of $L_1$ and $L_2$ independently comprises a chelating ligand comprising at least two metal coordinating atoms, where Y comprises a mono-coordinated diamine ligand, where X comprises one out of a second mono-coordinated diamine ligand and a nucleophilic ligand, where a is the total charge of the mono-coordinated ligand(s), where $An^-$ represents a lipophilic anion, where m is from 1 to p, and where $Z^-$ represents a second optional anion. Suitable chelating ligands include, but are not limited to, chelating ligands comprising at least two nitrogen atoms. According to some embodiments, the mono-coordinated ligand is chiral. The chirality may be (S)— or (R)—.

Suitable transition metals include, but are not limited to, cobalt (Co), iron (Fe), nickel (Ni), chromium (Cr), manganese (Mn), molybdenum (Mo), tungsten (W), rhenium (Re), ruthenium (Ru), technetium (Tc), osmium (Os), rhodium (Rh), iridium (Jr), platinum (Pt), and palladium (Pd). For example, according to some embodiments the transition metal is cobalt, iron, or nickel. Cobalt, iron, and nickel have the advantage of low cost. In some embodiments, the transition metal is cobalt. Suitable oxidation states of the transition metal include, but are not limited to, M(III) and M(IV).

Suitable lipophilic anions include, but are not limited to, tetrakis[(3,5-trifluromethyl)phenyl]borate); tetrakis[pentafluorophenyl]borate; carboranes of the general formula $CB_{11}H_{12}-$, and its derivatives; TRISPHAT of the general formula $P(O_2C_6C_{14})^{3-}$; and 1,1'-Binaphthyl-2,2'-diyl phosphates, and its derivatives.

Suitable conventional anions include, but are not limited to, $Cl^-$, perchlorate, and nitrate. The variable numbers p, m, n, a, b, and c are each integers. According to some embodiments, the transition metal complex is in hydrated form.

Transition Metal Complexes of Type 1
The Stereochemistry of the Chiral Ligand and the Chiral Metal Center Referring to FIG. 1, for the metal complexes, there exist two possible chiral configurations that center at the metal. These are called "chiral-at-metal centers" or "stereogenic metal centers". The configurations are named lambda (Λ) and delta (Δ). Representations of each configuration, Λ and delta Δ, are shown in FIG. 1, illustrated with 3 (5,5)-DPEN ligands and cobalt (Co) metal. Thus, shown in FIG. 1 are Λ-[Co((S,S)-dpen)$^3$]$^{3+}$ and Δ-[Co((S,S)-dpen)$_3$]$^{3+}$.

Figure 2:
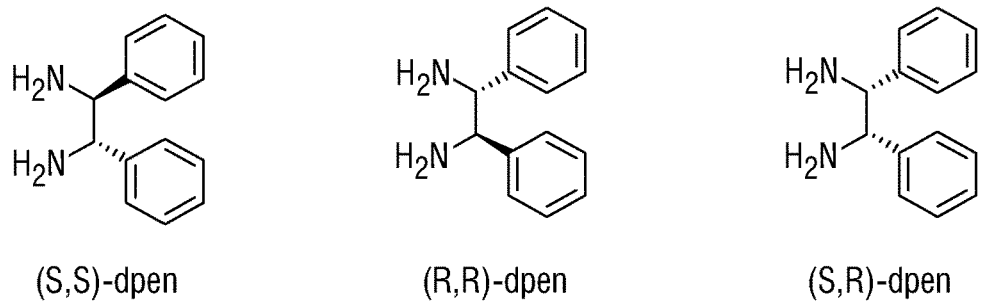
FIG. 2 represents three possible stereoisomeric arrangements for diphenylethylenediamine (DPEN): (S,S)-DPEN, (R,R)-DPEN, and (S,R)-DPEN.

Referring to FIG. 2, for diphenylethylenediamine (DPEN), 3 possible stereoisomeric arrangements are possible; (5,5)-DPEN, (R,R)-DPEN, and (S,R)-DPEN. Note that (R,S)-DPEN is equivalent to (S,R)-DPEN so listing it here, or otherwise herein, as a separate species is redundant.

Figure 3:
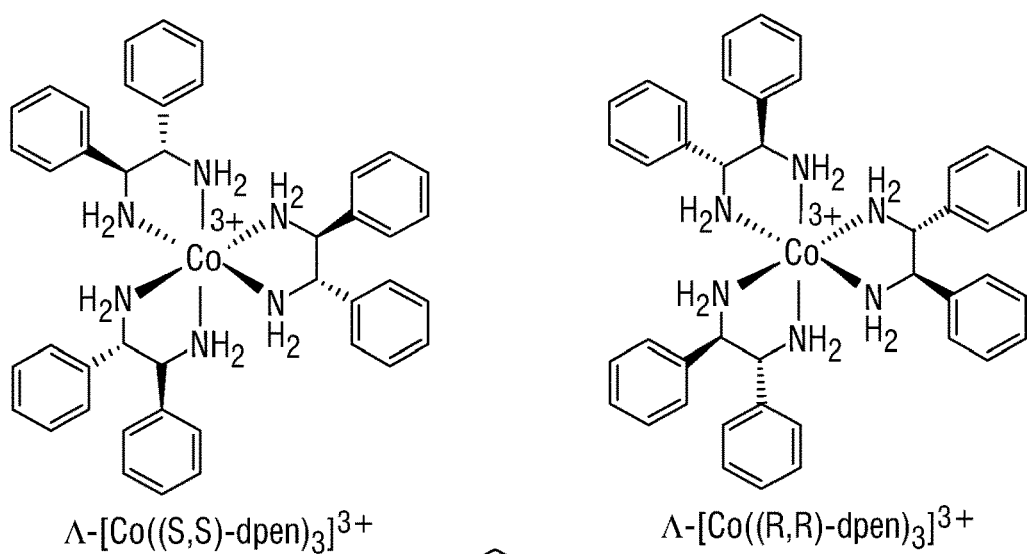
FIG. 3 shows the two configurations at the metal center, $\Lambda$ and $\Delta$, for each possible combination of the 3 chelating ligands.

Referring to FIG. 3, for each possible combination of the 3 chelating ligands there are two configurations at the metal center: Λ and Δ.

It will be understood that it is possible to use combinations of these 3 ligands within one compound, so the following list of compounds would also be available (not shown): 1) Λ-[Co((S,S)-dpen)$_2$((R,R)-dpen)]$^{3+}$; 2) Λ-[Co((S,S)-dpen)$_2$((S,R)-dpen)]$^{3+}$; 3) Λ-[Co((R,R)-dpen)$_2$((S,S)-dpen)]$^{3+}$; 4) Λ [Co((R,R)-dpen)$_2$((S,R)-dpen)]$^{3+}$; 5) Λ-[Co((S,R)-dpen)2((S,S)-dpen)]$^{3+}$; 6) Λ-[Co((S,R)-dpen)2((R,R)-dpen)]$^{3+}$; and 7) Λ-[Co((S,S)-dpen)((R,R)-dpen)((S,R)-dpen)]$^{3+}$.

Further, it will be understood that for all of these Λ complexes mentioned above, the corresponding Δ complex would also be available. Thus, the following list of compounds would also be available (not shown): 1) Δ-[Co((S,S)-dpen)$_2$((R,R)-dpen)]$^{3+}$; 2) Δ-[Co((S,S)-dpen)$_2$((S,R)-dpen)]$^{3+}$; 3) Δ-[Co((R,R)-dpen)$_2$((S,S)-dpen)]$^{3+}$; 4) Δ [Co((R,R)-dpen)$_2$((S,R)-dpen)]$^{3+}$; 5) Δ-[Co((S,R)-dpen)$_2$((S,S)-dpen)]$^{3+}$; 6) Δ-[Co((S,R)-dpen)$_2$((R,R)-dpen)]$^{3+}$; and 7) Δ-[Co((S,S)-dpen)((R,R)-dpen)((S,R)-dpen)]$^{3+}$.

Other Transition Metals

Besides cobalt, the other transition metals that could be used in a similar way in this catalysis include, but are not limited to, iron, nickel, chromium, manganese, molybdenum, tungsten, rhenium, ruthenium, technetium, osmium, rhodium, iridium, platinum, and palladium. Thus, according to some embodiments the transition metal is cobalt, iron, nickel, chromium, manganese, molybdenum, tungsten, rhenium, ruthenium, technetium, osmium, rhodium, iridium, platinum, or palladium. For example, according to some embodiments the transition metal is cobalt, iron, or nickel. Further, for example, according to some embodiments the transition metal is cobalt.

Counteranions

It is desirable for these catalysts to be soluble in aprotic organic solvents. This is accomplished by using counteranion pairings with the cationic cobalt complex that render the complex soluble in aprotic organic solvents. The counteranion pairings are an assembly of counter anion groups that render the cobalt cation soluble in organic solvents.

An Counteranions

Suitable assemblies use between 1 and 3 anions that are deemed, "lipophilic" or "organic soluble". In some embodiments, BArf-(tetrakis[(3,5-trifluromethyl)phenyl]borate) is a suitable anion. Other suitable lipophilic anions include, but are not limited to; tetrakis[pentafluorophenyl]borate; carboranes of the general formula $CB_{11}H^{12-}$, and its derivatives; TRISPHAT of the general formula $P(O_2C_6C_{14})^{3-}$; and 1,1'-Binaphthyl-2,2'-diyl phosphates, and its derivatives.

Z Counteranions

Often only one or two "organic soluble" anions are required in the package of 3 anions to render the whole complex soluble in aprotic organic solvents. In this case, the other one to two anion spaces can be filled by any possible anion even if it is not considered "lipophilic". Such anions include, but are not limited to; Hydride H—, Oxide $O^{2-}$, Fluoride $F^-$, Sulfide $S^{2-}$, Chloride $Cl^{31}$, Nitride $N^{3-}$, Bromide $Br^-$, Iodide $I^-$, Arsenate $AsO_4^{3-}$, Phosphate $PO_4^{3-}$, Arsenite $AsO_3^{3-}$, Hydrogen phosphate $HPO_4^{2-}$, Dihydrogen phosphate $H_2PO^{4-}$, Sulfate $SO_4^{2-}$, Nitrate $NO^{3-}$, Hydrogen sulfate $HSO^{4-}$, Nitrite $NO^{2-}$, Thiosulfate $S_2O_3^{2-}$, Sulfite $SO_3^{2-}$, Perchlorate $ClO^{4-}$, Iodate $IO^{3-}$, Chlorate $ClO^{3-}$, Bromate $BrO^{3-}$, Chlorite $ClO^{2-}$, Hypochlorite $OCl^-$, Hypobromite $OBr^-$, Carbonate $CO_3^{2-}$, Chromate $Cra_4^{2-}$, Hydrogen carbonate or Bicarbonate $HCO^{3-}$, Dichromate $Cr_2O_7^{2-}$, Acetate $CH_3COO^-$, formate $HCOO^-$, Cyanide $CN^-$, Amide $NH2^-$, Cyanate $OCN^-$, Peroxide $O^{22-}$, Thiocyanate $SCN^-$, Oxalate $C_2O_4^{2-}$, Hydroxide $OH^-$, Permanganate $MnO^{4-}$, Azide $N^{3-}$, and tartrate $C_4H_4O_6^{2-}$. Further suitable conventional anions include, but are not limited to, triflate $OSO_3CF^{3-}$ and tetraflouroborate $BF^{4-}$ and hexafluorophosphate $PF_6^-$.

Derivatives of the DPEN Ligand

It will be understood that derivatives of the above mentioned DPEN ligands may be used to make cobalt complexes. The stereochemistry rules that apply to the original DPEN ligands apply to the derivatives below. Further, the stereochemistry rules that apply to the metal centers of these complexes formed by the addition of these DPEN derivatives are the same as described above. For example, suitable DPEN derivatives include, but are not limited to, (S,S,)-, (R,R)-, and (S,R)-versions of 2-bis-(4-methoxyphenyl)-1,2-diaminoethane; 2-bis-(4-chlorophenyl)-1,2-diaminoethane; 2-bis-(4-trifluoromethylphenyl)-1,2-diaminoethane; 2-bis-(4-nitrophenyl)-1,2-diaminoethane; 2-bis-(1-napthyl)-1,2-diaminoethane; 2-bis-(2-napthyl)-1,2-diaminoethane; 1,2-bis(2-methoxyphenyl)ethane-1,2-diamine; 1,2-bis(3-methoxyphenyl)ethane-1,2-diamine; 1,2-bis(2-methylphenyl)ethane-1,2-diamine; 1,2-bis(3-methylphenyl)ethane-1,2-diamine; 1,2-bis(4-methylphenyl)ethane-1,2-diamine; 1,2-di(pyridin-2-yl)ethane-1,2-diamine; 1,2-di(pyridin-3-yl)ethane-1,2-diamine; 1,2-di(pyridin-4-yl)ethane-1,2-diamine; 1,2-bis-(4-methoxyphenyl)-1,2-diaminoethane; 1,2-bis-(4-chlorophenyl)-1,2-diaminoethane; 1,2-bis-(4-trifluoromethylphenyl)-1,2- diaminoethane; 1,2-bis-(4-nitrophenyl)-1,2-diaminoethane; 1,2-bis-(1-napthyl)-1,2-diaminoethane; and 1,2-bis-(2-napthyl)-1,2-diaminoethane.

Other Ligands

Figure 32:
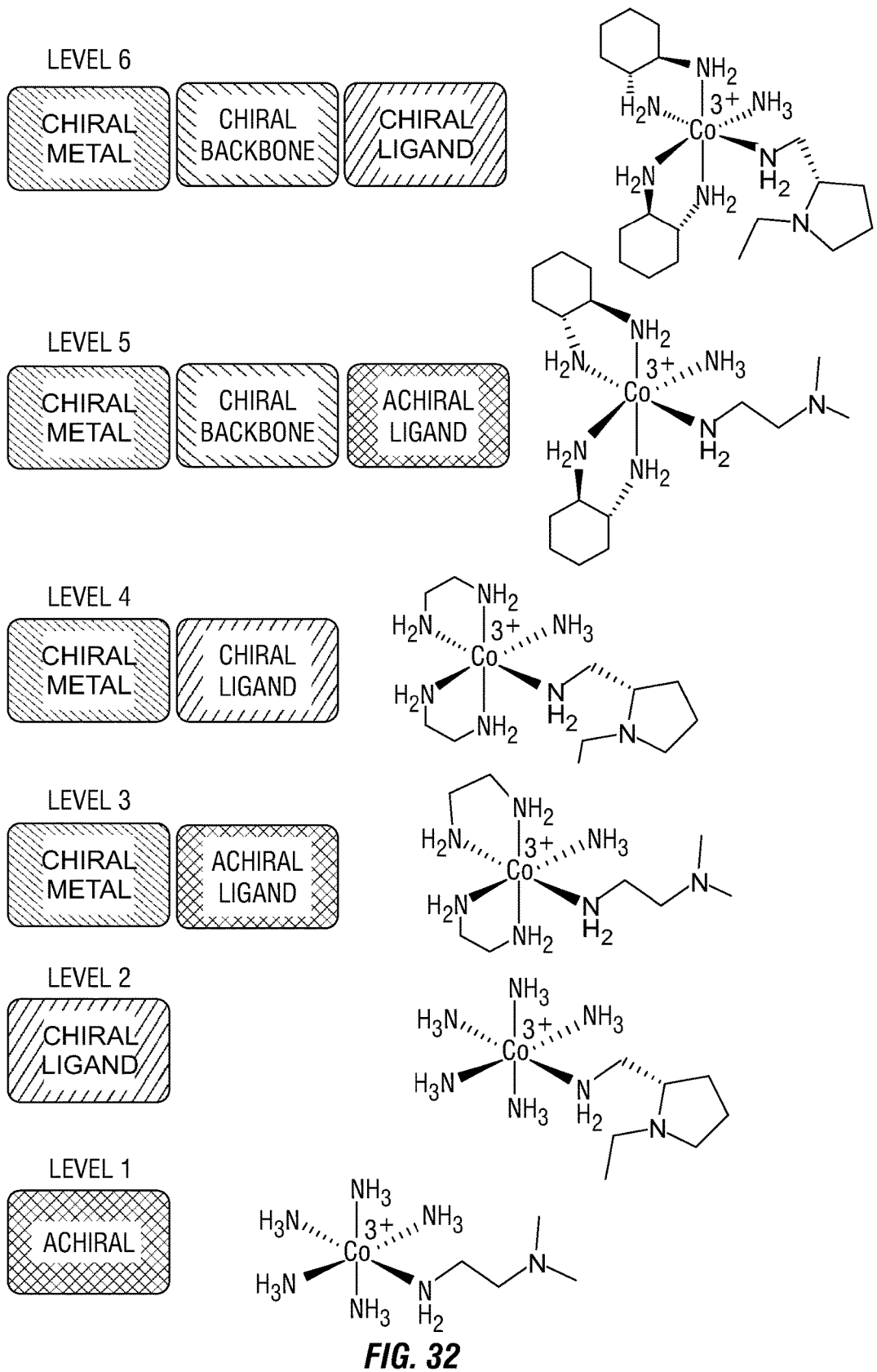
FIG. 32 illustrates an example of possible arrangements of ligands coordinated to a metal in a Type 3 transition metal complex.

It will be understand that other substituted diamines may be used to make the complex. Referring to FIG. 32, the substituted diamine may be cyclohexanediamine.

Transition Metal Complexes of Type 2

Stereochemistry of the Chiral Ligand and the Chiral Metal Center

Figure 8:
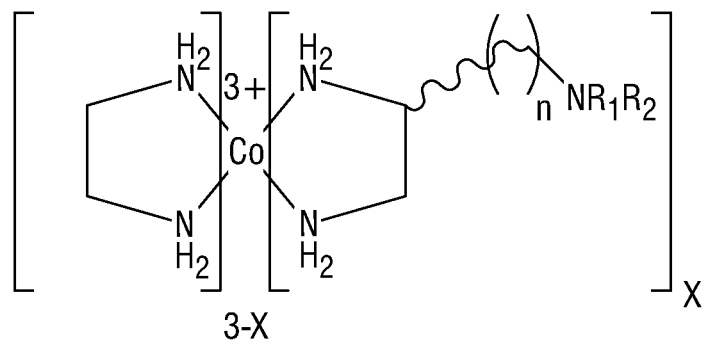
FIG. 8 shows various Type 2 transition metals (cobalt amine) complexes with cationic backbone prepared using a substituted chiral ethylene diamine ligands having a pendant Lewis base in its side arm. X is the amount of the substituted chiral ethylene diamine ligands having a pendant Lewis base in its side arm.

Referring to FIG. 8, various cobalt amine complexes having the following cationic backbone can be prepared using a substituted chiral ethylene diamine ligands having a pendant Lewis base in its side arm. Still referring to FIG. 8, X is the amount of the substituted chiral ethylene diamine ligands having a pendant Lewis base in its side arm.

Figure 9:
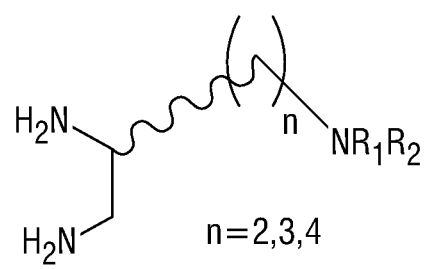
FIG. 9 shows a series of substituted chiral ethylene diamine ligands, having pendant Lewis base in its side arm.

Referring to FIG. 9, a series of substituted chiral ethylene diamine ligands, having pendant Lewis base in its side arm can be synthesized. In particular, the ligand may be $EN(CH_2)_nNR_1R_2$.

Figure 10:
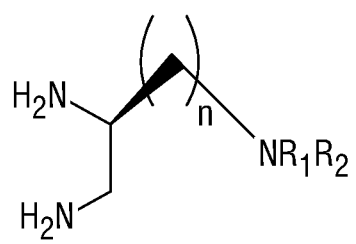
FIG. 10 shows ligands with possible (S) configuration and (R) configuration at the chiral center.
Figure 10:
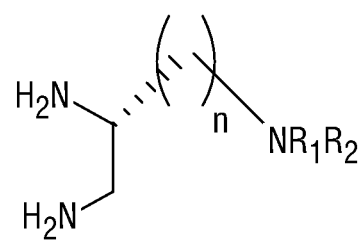
Figure 11:
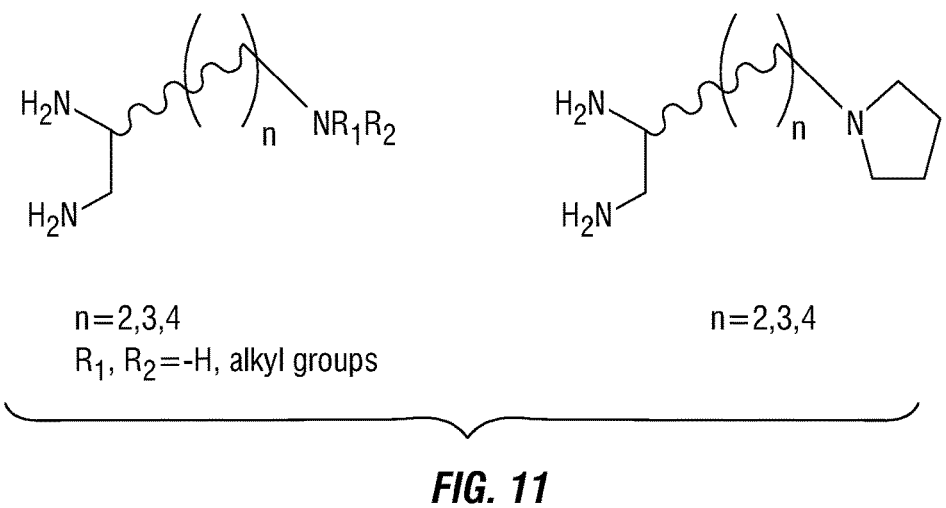
FIG. 11 shows variation, in length of the tether and wide variety of basic functional moieties incorporated into the ligands, to tune the basicity of the Lewis base.

Referring to FIG. 10, these ligands can have (S) configuration and (R) configuration at the chiral center. Referring to FIG. 11, for these ligands, the length of the tether can be varied and a wide variety of basic functional moieties can be incorporated to tune the basicity of the Lewis base.

When X=1

Figure 12:
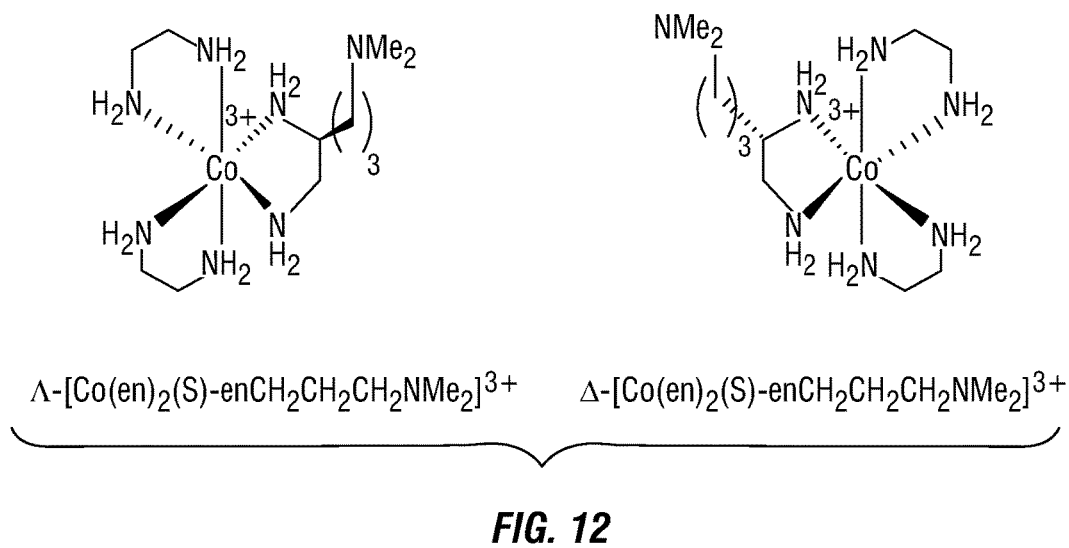
FIG. 12 shows that the two stereoisomers (or diastereomers) that the cobalt complex (X=1) can exist in, when the ligand has (S) configuration in the chiral center, n=3 and $R_1=R_2=Me$.

Referring to FIG. 12, when the ligand has (S) configuration in the chiral center, n=3 and R1=R2=Me, then the cobalt complex (X=1) can exist as two stereoisomers (or diastereomers) which are shown in the following.

Figure 13:
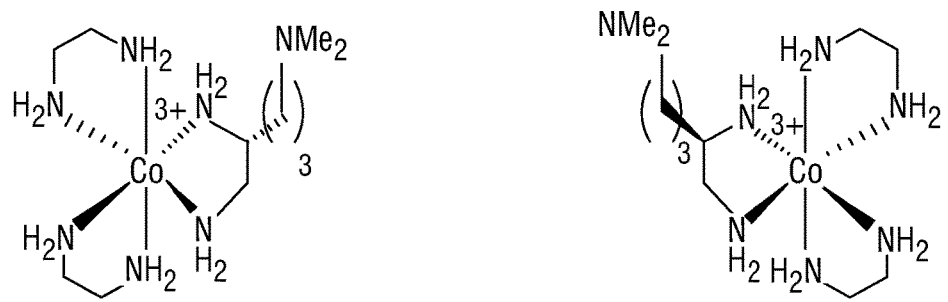
FIG. 13 shows $\Lambda$ and $\Delta$ stereoisomers (or diastereomers) of the cobalt complex with the ligand which has (R) configuration in the chiral center.

Referring to FIG. 13, similarly, with the ligand which has (R) configuration in the chiral center, the cobalt complexes also show Λ and Δ stereoisomers (or diastereomers).

When X=2

Figure 14:
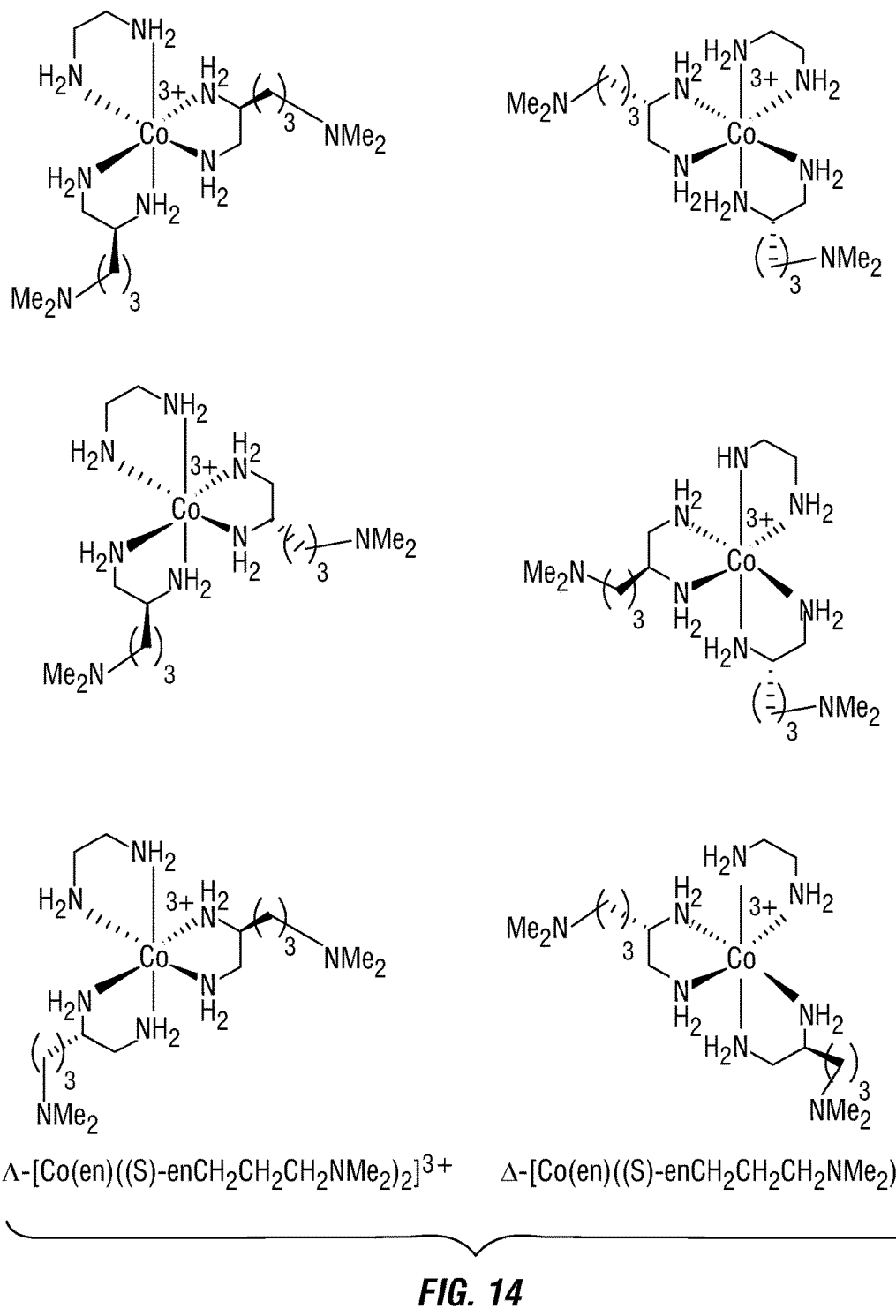
FIG. 14 shows the six stereoisomers (or diastereomers) of the cobalt complex (X=2), when the ligand has (S) configuration in the chiral center, n=3 and $R_1=R_2=Me$. The three $\Lambda$ isomers are shown on the left and three $\Delta$ isomers are shown in the right.

Referring to FIG. 14, when the ligand has (S) configuration in the chiral center, n=3 and R1=R2=Me, then the cobalt complex (X=2) may have six stereoisomers (or diastereomers). The three Λ isomers are shown on the left and three Δ isomers are shown on the right.

The cobalt complex (X=2) may also have six stereoisomers (or diastereomers) when the same ligand with (R) configuration at the chiral center has been used.

When X=3

Figure 15:
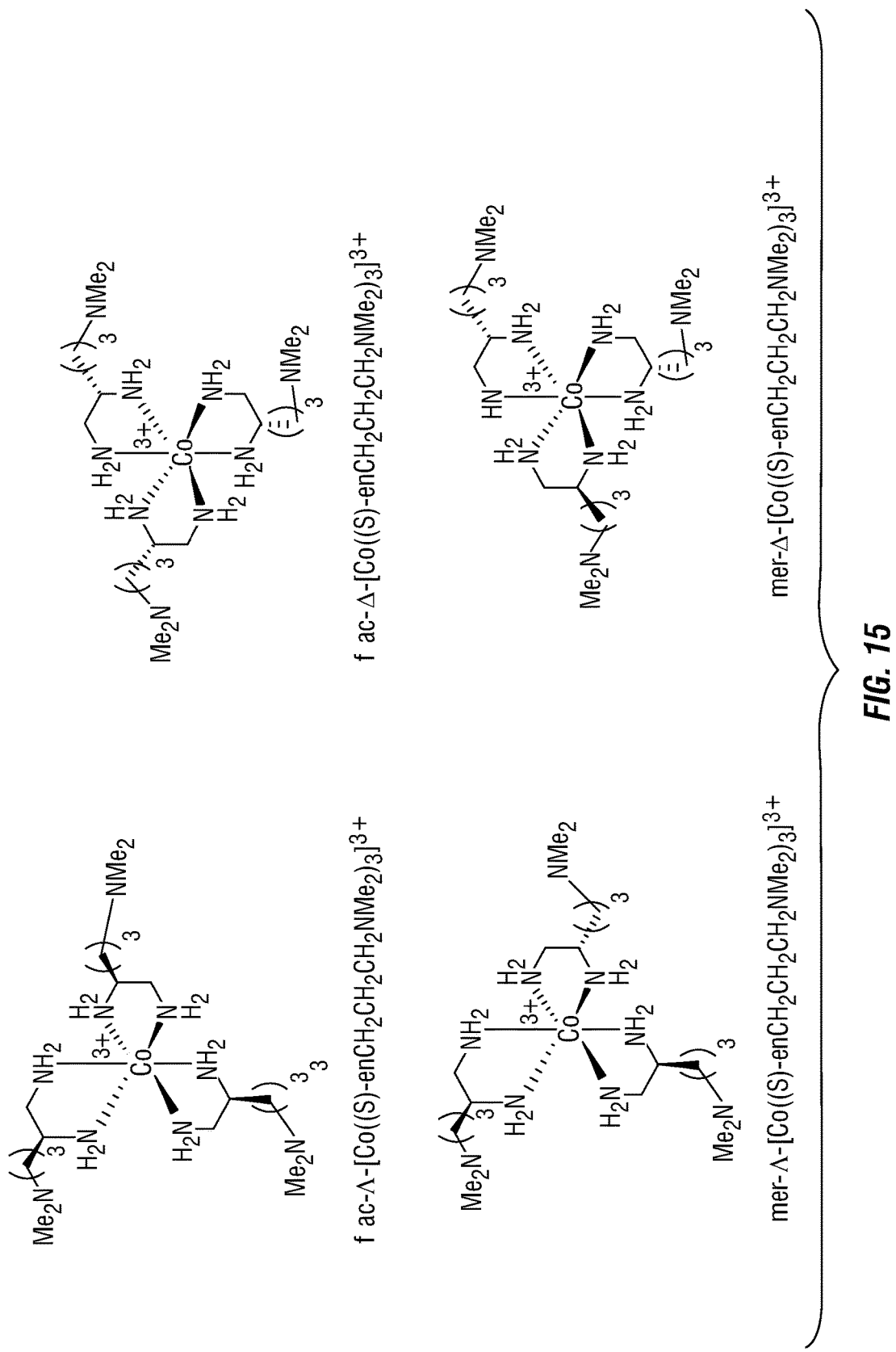
FIG. 15 shows the four different stereoisomers (or diastereomers) possible when cobalt is attached to three ligands (X=3) with (S) configuration in the chiral center, n=3 and $R_1=R_2=Me$.

Referring to FIG. 15, four different stereoisomers (or diastereomers) are possible when cobalt is attached to three ligands (X=3) with (S) configuration in the chiral center, n=3 and R1=R2=Me, which are shown in the following.

Four other stereoisomers (or diastereomers) of the cobalt complex may also be possible when the same ligand with (R) configuration at the chiral center has been used.

Other Transition Metals

Besides cobalt, the other transition metals that could be used in a similar way in this catalysis include, but are not limited to, iron, nickel, chromium, manganese, molybdenum, tungsten, rhenium, ruthenium, technetium, osmium, rhodium, iridium, platinum, and palladium. Thus, according to some embodiments, the transition metal is cobalt, iron, nickel, chromium, manganese, molybdenum, tungsten, rhenium, ruthenium, technetium, osmium, rhodium, iridium, platinum, or palladium. For example, according to some embodiments, the transition metal is cobalt, iron, or nickel. Further, for example, according to some embodiments, the transition metal is cobalt.

The Counteranions

It is desirable for these catalysts to be soluble in aprotic organic solvents. This is accomplished by using counteranion pairings with the cationic cobalt complex that render the complex soluble in aprotic organic solvents. The counteranion pairings are an assembly of counter anion groups that render the cobalt cation soluble in organic solvents.

An Counteranions

Suitable assemblies use between 1 and 3 anions that are deemed "lipophilic" or "organic soluble". BArf-(tetrakis[(3,5-trifluromethyl)phenyl]borate) is a suitable anion. Further, other suitable lipophilic anions include, but are not limited to; tetrakis[pentafluorophenyl]borate; carboranes of the general formula $CB_{11}H^{12-}$, and its derivatives; TRISPHAT of the general formula $P(O_2C_6Cl_4)^{3-}$; and 1,1'-Binaphthyl-2,2'-diyl phosphates, and its derivatives.

Z Counteranions

Often only one or two "organic soluble" anions are required in the package of 3 anions to render the whole complex soluble in aprotic organic solvents. In this case, the other one to two anion spaces can be filled by any possible anion even if it is not considered "lipophilic". Such anions include, but are not limited to; Hydride $H^-$, Oxide $O^{2-}$, Fluoride $F^-$, Sulfide $S^{2-}$, Chloride $Cl^-$, Nitride $N^{3-}$, Bromide $Br^-$, Iodide $I^-$, Arsenate $AsO_4^{3-}$, Phosphate $PO_4^{3-}$, Arsenite $AsO^{33-}$, Hydrogen phosphate $HPO_4^{2-}$, Dihydrogen phosphate $H_2PO^{4-}$, Sulfate $SO4^{2-}$, Nitrate $NO^{3-}$, Hydrogen sulfate $HSO^{4-}$, Nitrite $NO^{2-}$, Thiosulfate $S_2O_3^{2-}$, Sulfite $SO_3^{2-}$, Perchlorate $ClO^{4-}$, Iodate $IO^{3-}$, Chlorate $ClO^{3-}$, Bromate $BrO^{3-}$, Chlorite $ClO^{2-}$, Hypochlorite $OCl^-$, Hypobromite $OBr^-$, Carbonate $CO_3^{2-}$, Chromate $CrO_4^{2-}$, Hydrogen carbonate or Bicarbonate $HCO^{3-}$, Dichromate $Cr_2O_7^{2-}$, Acetate $CH_3COO^-$, formate $HCOO^-$, Cyanide $CN^-$, Amide $NH2^-$, Cyanate $OCN^-$, Peroxide $O^{22-}$, Thiocyanate $SCN^-$, Oxalate $C_2O_4^{2-}$, Hydroxide $OH^-$, Permanganate $MnO^{4-}$, Azide $N^{3-}$, and tartrate $C_4H_4O_6^{2-}$. Further suitable conventional anions include, but are not limited to, triflate $OSO_3CF^{3-}$, tetraflouroborate $BF^{4-}$ and hexafluorophosphate $PF6^-$.

Transition Metal Complexes of Type 3

Stereochemistry of the Chiral Metal Center

Figure 30:
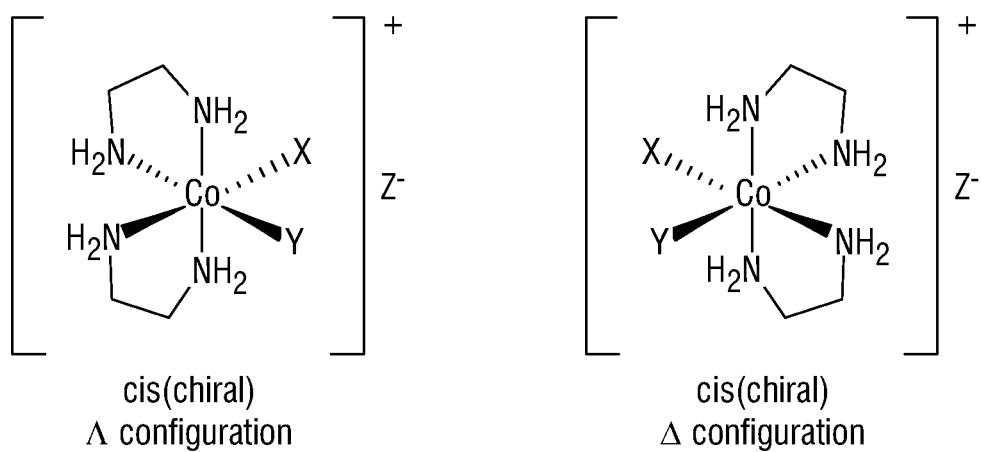
FIG. 30 depicts the Type 3 transition metal complex in cis configuration which is considered a "chiral-at-metal metal center" or "stereogenic metal center". The minimum requirement for an octahedral (6 binding sites) metal complex is to have 2 chelating ligands in the cis configuration (chelating means one ligand binds at two different sites). The metal is a chiral center in the cis configuration whenever X=Y or when X≠Y.

Referring to FIG. 30, the minimum requirement for there to be a "chiral metal center" or "stereogenic metal center" is for an octahedral (6 binding sites) metal complex to have 2 chelating ligands in the cis configuration (chelating means one ligand binds at two different sites). The metal is a chiral center in the cis configuration whenever X=Y or when X≠Y.

Figure 31:
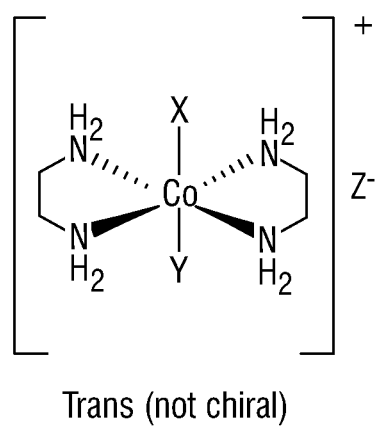
FIG. 31 depicts the Type 3 transition metal complex with trans configuration which is never considered a "chiral-at-metal" center.

Referring to FIG. 31, the complex with trans configuration is never considered a "chiral-at-metal" center. However, if X or Y is a ligand with a chiral center then the whole complex is considered chiral.

Hierarchy of Chiral Metal Complexes

Referring to FIG. 32, a pictorial example of possible arrangements of ligands coordinated to a metal is shown. Each level with a chiral metal is drawn as Λ but may also exist as Δ. Each chiral backbone (chelating ligand) is drawn as (R,R) but could also exist as (R,S) and (S,S). Finally, each ligand that has a stereocenter is drawn as (S) but could also be drawn as (R).

Chelating Ligand

Figure 33:
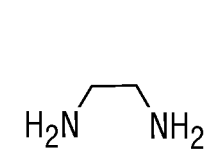
FIGS. 33-34 show that the chelating ligand can take several shapes in a Type 3 transition metal complex. Nitrogen is illustrative of a metal coordinating element.
Figure 33:
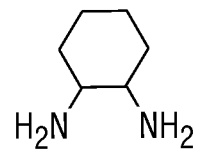
Figure 33:
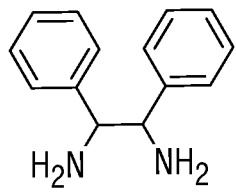
Figure 33:
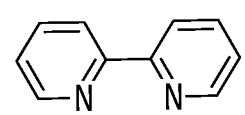
Figure 33:
Figure 34:
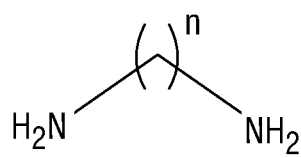

Referring to FIGS. 33 and 34, the chelating ligand can take several shapes. The unifying theme is that the ligand has at least 2 nitrogen atoms. Nitrogen is illustrative of a metal coordinating element. Thus, the ligand may have at least 2 metal coordinating atoms.

Ligands X and Y

The X and Y ligands may be the same or they may be different. At least one of X and Y is a diamine. In some embodiments, one amine of the diamine coordinates to the metal while the other amine remains uncoordinated.

Figure 35:
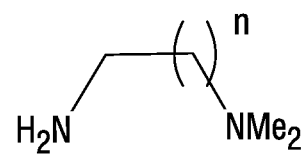
FIGS. 35-36 show examples of X and Y ligands of Type 3 transition metal complexes. At least one of X and Y is a diamine. The diamine can be achiral (FIG. 35) or chiral (FIG. 36)
Figure 36:
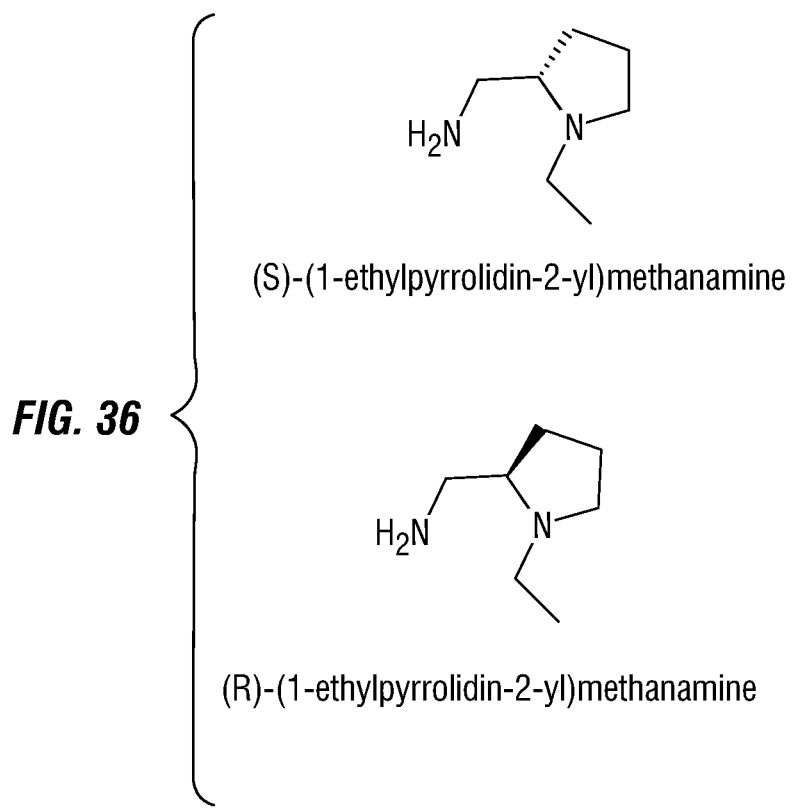

Referring to FIGS. 35 and 36, examples of these ligands are shown. The diamine can be achiral (FIG. 35) or chiral (FIG. 36). One unifying theme is that the two amines in one diamine ligand are different. One of these is a primary amine (1° amine) because it is bonded to 1 carbon and 2 hydrogens. The other amine on the ligand is a tertiary amine (3° amine) because it is bonded to 3 carbons. Ligands with a 1° amine and 2° amine (bonds to 2 carbons and 1 hydrogen) are also contemplated.

Metal Complexes

Figure 37:
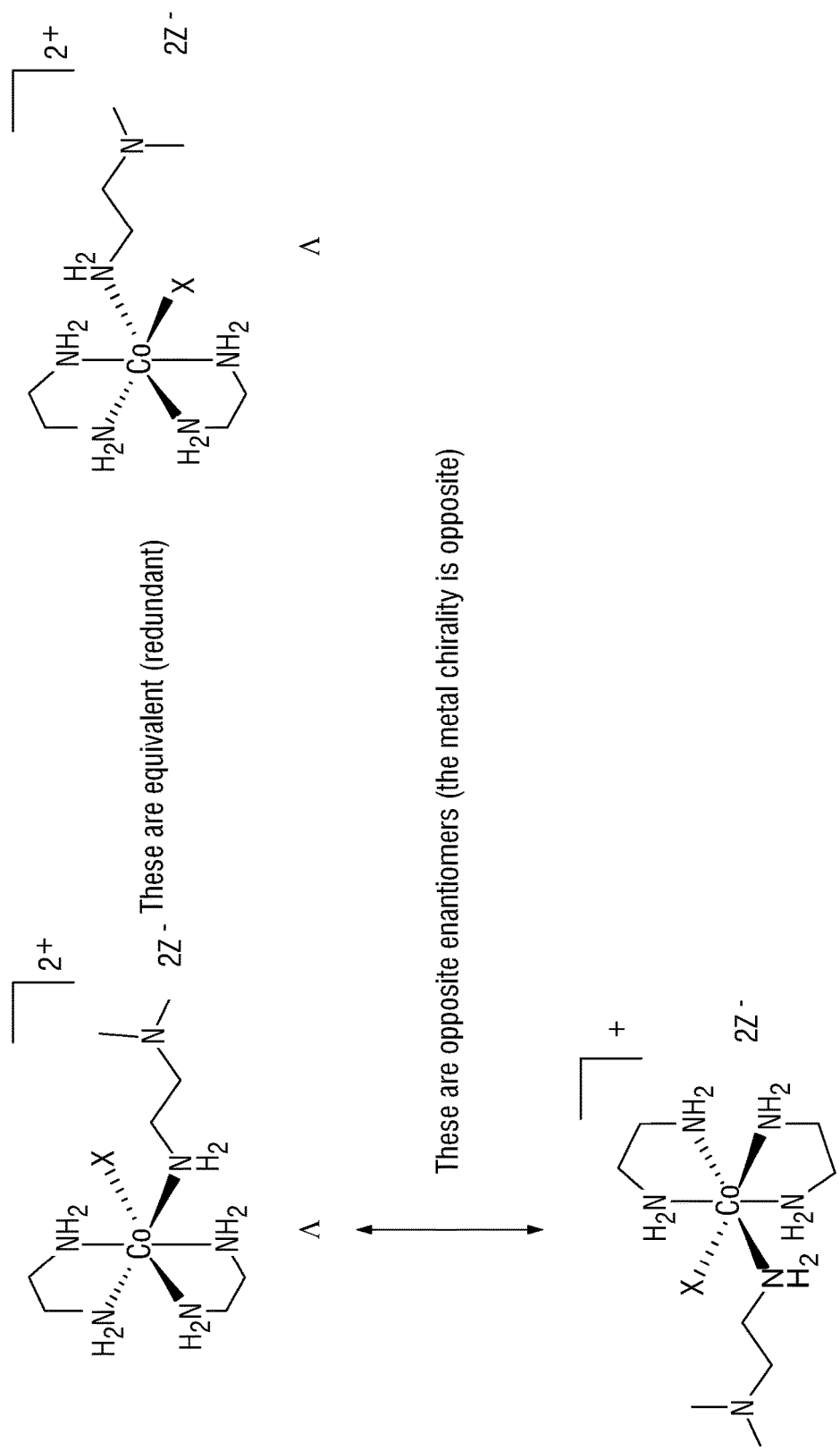
FIG. 37 shows a typical Type 3 transition metal complex.

FIG. 37 represents a typical complex. In this embodiment, for any combination of ligands X and Y, there are only two possible configurations Λ and Δ. The remaining X ligand can be anything including another 1°/3° amine ligand. In some embodiments, this X spot is occupied by chloride ($Cl^-$) or ammonia ($NH_3$).

Other Transition Metals

Besides cobalt, the other transition metals that could be used in a similar way in this catalysis include, but are not limited to, iron, nickel, chromium, manganese, molybdenum, tungsten, rhenium, ruthenium, technetium, osmium, rhodium, iridium, platinum, and palladium. Thus, according to some embodiments the transition metal is cobalt, iron, nickel, chromium, manganese, molybdenum, tungsten, rhenium, ruthenium, technetium, osmium, rhodium, iridium, platinum, or palladium. For example, according to some embodiments, the transition metal is cobalt, iron, or nickel. Further, for example, according to some embodiments, the transition metal is cobalt.

The Counteranions

It is desirable for these catalysts to be soluble in aprotic organic solvents. This is accomplished by using counteranion pairings with the cationic cobalt complex that render the complex soluble in aprotic organic solvents. The counteranion pairings are an assembly of counter anion groups that render the cobalt cation soluble in organic solvents.

An Counteranions

Suitable assemblies use between 1 and 3 anions that are deemed "lipophilic" or "organic soluble". Barf-(tetrakis[(3,5-trifluromethyl)phenyl]borate) is a suitable anion. Further, other suitable lipophilic anions include, but are not limited to; tetrakis[pentafluorophenyl]borate; carboranes of the general formula $CB_{11}H^{12-}$, and its derivatives; TRISPHAT of the general formula $P(O_2C_6C_{14})^{3-}$; and 1,1'-Binaphthyl-2,2'-diyl phosphates, and its derivatives.

Z Counteranions

In some embodiments, one or two "organic soluble" anions are required in the package of 3 anions to render the whole complex soluble in aprotic organic solvents. In such embodiments, the other one to two anion spaces can be filled by any possible anion even if it is not considered "lipophilic". Such anions include, but are not limited to; Hydride $H^-$, Oxide $O^{2-}$, Fluoride $F^-$, Sulfide $S^{2-}$, Chloride $Cl^-$, Nitride $N^{3-}$, Bromide $Br^-$, Iodide $I^-$, Arsenate $AsO_4^{3-}$, Phosphate $PO_4^{3-}$, Arsenite $AsO^{33-'}$ Hydrogen phosphate $HPO4^{2-}$, Dihydrogen phosphate $H2PO^{4-}$, Sulfate $SO4^{2-}$, Nitrate $NO^{3-}$, Hydrogen sulfate $HSO^{4-}$, Nitrite $NO^{2-}$, Thiosulfate $S_2O^{32-}$, Sulfite $SO^{32-}$, Perchlorate $ClO^{4-}$, Iodate $IO^{3-}$, Chlorate $ClO^{3-}$, Bromate $BrO^{3-}$, Chlorite $ClO^{2-}$, Hypochlorite $OCl^-$, Hypobromite $OBr^-$, Carbonate $CO^{32-}$, Chromate $CrO^{42-}$, Hydrogen carbonate or Bicarbonate $HCO^{3-}$, Dichromate $Cr_2O^{72-}$, Acetate $CH3COO^-$, formate $HCOO^-$, Cyanide $CN^-$, Amide $NH^{2-}$, Cyanate $OCN^-$, Peroxide $O^{22-}$, Thiocyanate $SCN^-$, Oxalate $C_2O_4^{2-}$, Hydroxide $OH^-$, Permanganate $MnO^{4-}$, Azide $N^{3-}$, and tartrate $C_4H_4O_6^{2-}$. Further suitable conventional anions include, but are not limited to, triflate $OSO_3CF^{3-}$, tetraflouroborate $BF^{4-}$ and hexafluorophosphate $PF6^-$.

Applications and Advantages

The transition metal complexes of the present disclosure provide an attractive low cost catalyst system for the commercial manufacture of enantiopure chemicals. In various embodiments, the transition metal complexes of the present disclosure are highly enantioselective and stable. Further, the transition metal complexes of the present disclosure can be synthesized and separated as pure diastereomers on a gram scale. These have the added advantage of being easily tunable electronic and steric factors with modified DPEN ligands. Further, the transition metal complexes of the present disclosure demonstrate unique features compared to other hydrogen bond mediated catalysts, for example improved function in polar solvents or aqueous media.

Additional Embodiments

Reference will now be made to various embodiments of the present disclosure and experimental results that provide support for such embodiments. Applicants note that the disclosure herein is for illustrative purposes only and is not intended to limit the scope of the claimed subject matter in any way.

EXAMPLE 1

Type 1 Transition Metal Complexes
Preparation of DPEN Ligand Derivatives

Figure 4:
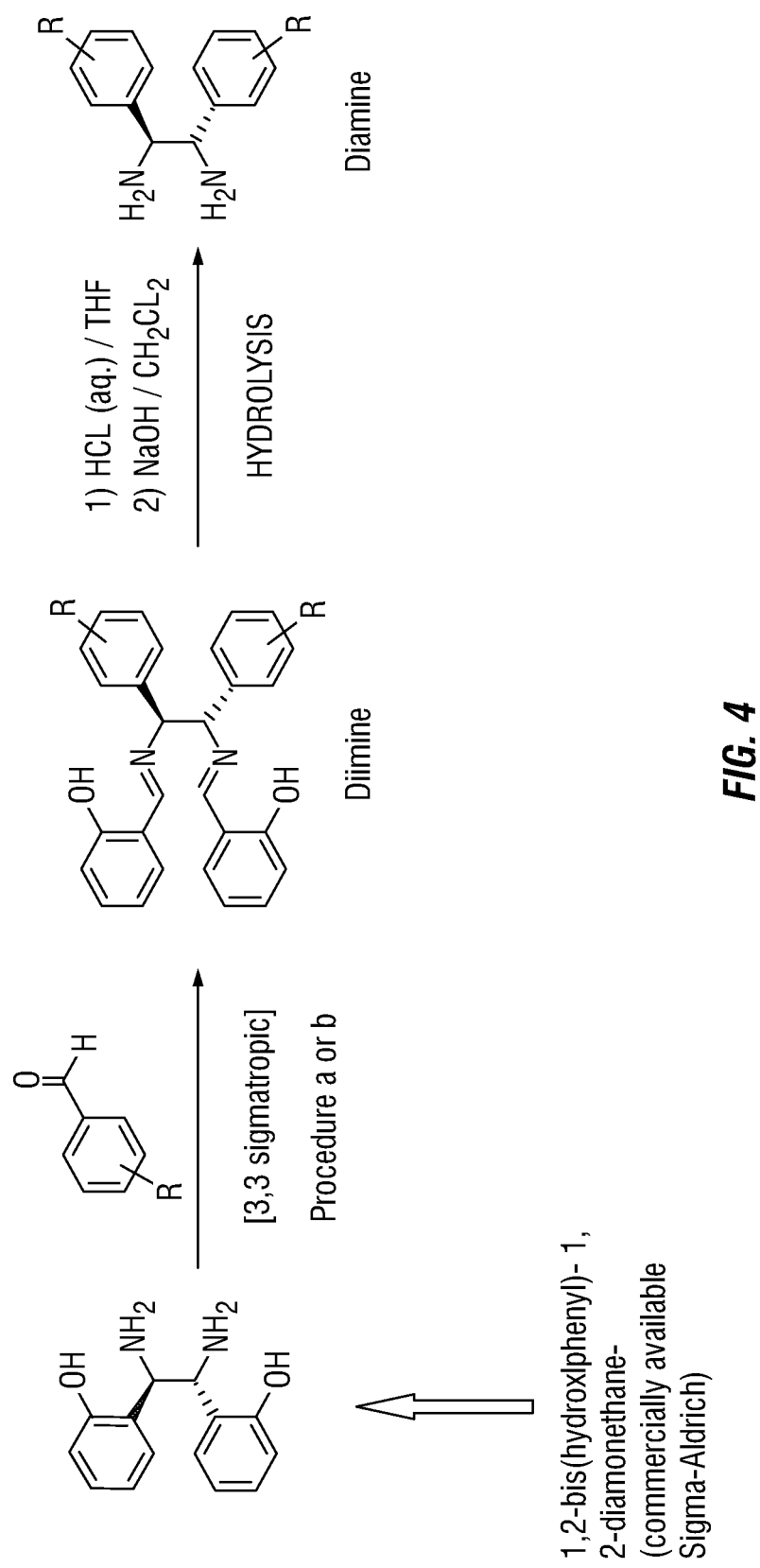
FIG. 4 illustrates a procedure to prepare derivatives of DPEN ligand.
Figure 5A:
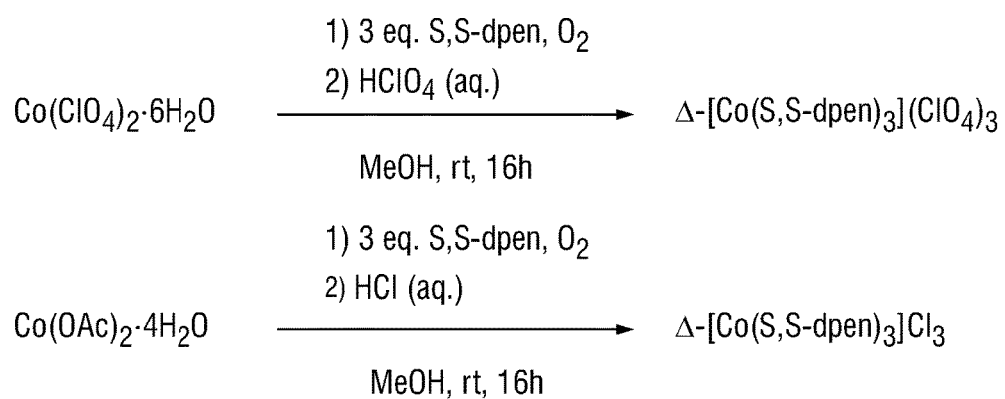
FIGS. 5A-5B illustrate a general procedure to prepare DPEN ligand derivatives, where
Figure 5B:
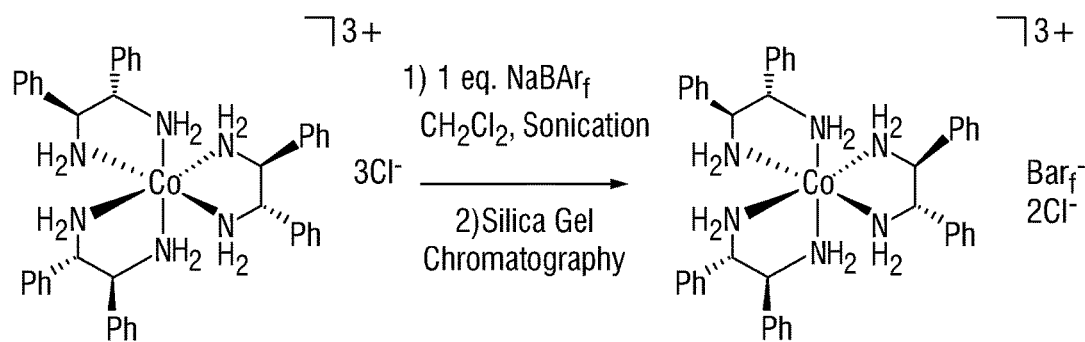

Referring to FIG. 4, a procedure to prepare derivatives of the DPEN ligand is illustrated. It is a general procedure that works to make a large number of DPEN derivatives. In principle, the choice of aldehydes with different variable groups (denoted as R) gives the different derivatives of the DPEN ligand. It will be understood that there is more than one procedure to prepare these derivatives of the DPEN ligand. The procedure illustrated in FIG. 5 is slightly modified from that offered by: Kim, H.; Nguyen, Y.; Yen, C. P. H.; Chagal, L.; Lough, A. J.; Kim, B. M.; Chin, J. J. Am. Chem. Soc. 2008, 130, 12184-12191.

EXAMPLE 2

Preparation of Transition Metal Complexes

Referring to FIG. 5, a general procedure to prepare cobalt complexes is illustrated. Part A illustrates a procedure to form an intermediate cobalt complex with conventional anions from a precursor cobalt salt, where the anion of the intermediate cobalt complex is the same as the anion of the precursor cobalt salt. Part B illustrates a procedure to form a cobalt complex soluble in organic solvent by replacing at least one of the conventional anions with a lipophilic anion.

Preparation of DPEN Ligand Derivatives

Procedure A.

To a cloudy solution of 0.9 g (4.10 mmol) of 1,2-bis (hydroxylphenyl)-1,2-diamonoethane in ethanol (30 mL) was added (9.84 mmol, 2.4 eq.) of the corresponding aldehyde. The resulting clear solution was stirred at room temperature overnight during which time a yellow precipitate develops. The solid is collected by filtration, washed with ethanol, and dried in vacuum.

Or

Procedure B.

To a clear solution of 0.9 g (4.10 mmol) of 1,2-bis (hydroxylphenyl)-1,2-diamonoethane in DMSO (30 mL) as added (9.84 mmol, 2.4 eq.) of the corresponding aldehyde. The resulting mixture was stirred at room temperature overnight and then the mixture was poured into distilled water (150 mL). The aqueous layer was extracted with diethyl ether (3×100 mL) and the organic layers were dried over $Na_2SO_4$, filtered, and concentrated by rotovap. The resulting diimine was further dried by oil pump vacuum.

EXAMPLE 3

Hydrolysis of the Diimine Products Formed by Either Procedure A or B

The diimine products from either procedure A or B were dissolved in THF (30 mL) and aqueous HCl (3 mL, 12 M) was added. The mixture stirred at room temperature for 3 hours then was partitioned between $H_2O$ (100 mL) and $CH_2Cl_2$ (100 mL). The organic phase was removed and the aqueous phase washed with $CH_2Cl_2$ (100 mL). The aqueous phase was made basic by slow addition of 3 M NaOH. The resulting cloudy solution was extracted with $CH_2Cl_2$ (3×150 mL). The organic phases were dried over $Na_2SO_4$, filtered, and concentrated by rotovap. The resulting diamines are further dried by oil pump vacuum.

The following list of DPEN derivatives have been prepared by this method: (S,S)-2-bis-(4-methoxyphenyl)-1,2-diaminoethane (procedure A); (S,S)-2-bis-(4-chlorophenyl)-1,2-diaminoethane (procedure B) (S,S)-2-bis-(4-trifluoromethylphenyl)-1,2-diaminoethane (procedure B); (S,S)-2-bis-(4-nitrophenyl)-1,2-diaminoethane (procedure A); (S,S)-2-bis-(1-napthyl)-1,2-diaminoethane (procedure B); and (S,S)-2-bis-(2-napthyl)-1,2-diaminoethane (procedure B).

EXAMPLE 4

Preparation of Transition Metal Complexes

Procedures for the synthesis of cobalt complexes are illustrated in the example below. These 2 procedures are generally representative for any DPEN ligand set (i.e. a DPEN ligand or DPEN derivative of any stereochemistry could be substituted in this procedure). The only difference between the two procedures is whether the end product is a Λ or Δ metal complex.

Procedure 1. Λ-[Co(dpen)3](BArf)Cl2 (Λ-1)

Cobalt acetate tetrahydrate (0.601 g, 2.49 mmol) and (S,S)-dpen (1.61 g, 7.60 mmol, 3.32 eq.) were dissolved in methanol (75 mL) and charcoal (0.1 g) was added. Air was passed through the vigorously stirred suspension at room temperature for 16 hours. The suspension was filtered through a pad of celite and the bright orange filtrate was acidified with aqueous HCl (2M, 2 mL). The solvents were gently evaporated in an oil bath at 45° C. under a stream of nitrogen until the volume reached ca. 10 mL. The remaining solid was suspended in methanol (30 mL) and water (100 mL) and filtered. The residue was suspended and filtered three times from hot acetone (30 mL) The bright orange solid was dried under oil pump vacuum to yield the trichloride salt (0.708 g).

A portion of the orange solid (0.452 g) was suspended in dichloromethane (10 mL) and NaBArf (0.501 g, 0.5655 mmol) was added. The suspension was mixed by sonication and the colorless dichloromethane rapidly turned bright orange as a faint white precipitate of NaCl developed. The new suspension was filtered and the filtrate loaded onto a silica gel column. The sorbed orange band was washed with $CH_2Cl_2$ (100 mL) and then was eluted with 98.5/1.5 $CH_2Cl_2$:MeOH. A very faint green band elutes first followed by a singular intense orange band. The orange band is collected and concentrated by rotary evaporation and further dried under oil pump vacuum for 15 hours to yield a bright orange solid (0.659 g).

1H NMR ($CD_2Cl_2$, 500 MHz) δ 8.30 (br s, NH, 6H), 7.74 (s, o-CH BArf-, 8H), 7.56 (s, p-CH BArf-, 4H), 7.41 (t, 6.5 Hz, p-CH dpen, 6H), 7.35 (t, 7.5 Hz, m-CH dpen, 12 H), 7.30 (d, 8.0 Hz, o-CH dpen, 12 H) 4.48 (s, CH, dpen, 6H), 3.82 (br s, NH, 6H), 2.18 (br s, $H_2O$, 3H), 1.80 (s, HOD, 3 H). 13C NMR ($CD_2Cl_2$, 125 MHz) for BArf-δ 161.7 (q, 1JBC=49.4 Hz, i), 134.8 (s, o), 128.8 (q, 2JCF=31.0 Hz, m), 124.5 (q, 1JCF=270.9 Hz, CF3), 117.4 (s, p), for dpen 133.9 (s), 130.7 (s), 130.1 (s), 127.4 (s), 63.0 (s, PhCHNH$_2$)

Procedure 2. Δ-[Co(dpen)3](BArf)Cl2

Cobalt perchlorate hexahydrate (0.233 g, 0.775 mmol) and S,S-dpen (0.496 g, 2.33 mmol, 3.01 eq.) were dissolved in MeOH (50 mL) and charcoal (0.1 g) was added. Air was passed through the vigorously stirred suspension at room temperature for 16 hours. The mixture was filtered through celite and the filtrate acidified with $HClO_4$ (2 mL, 35% in $H_2O$). The methanol was gently evaporated by heating in an oil bath to 45° C. under a stream of nitrogen. A brownish yellow precipitate developed when most of the MeOH had been removed. A suspension was made by adding $H_2O$ (100 mL) which was filtered and washed with more $H_2O$ (100 mL). The residue was then dissolved in MeOH (50 mL) and sorbed on a Dowex cation exchange column. The orange band was washed with 1:1 $H_2O$/MeOH (100 mL). The orange band was eluted with increasing gradients of aqueous HCl in methanol; 1M aq. HCl in MeOH (100 mL), 2M aq. HCl in MeOH (100 mL), 3M aq. HCl in MeOH (100 mL), 4M aq. HCl in MeOH (200 mL). At 4M HCl, the orange band elutes from the column. The collected fraction is concentrated by a rotary evaporator equipped with a base trap to yield a bright orange solid as the crude trichloride (0.155 g). A portion of this solid (0.103 g) was suspended in $CH_2Cl_2$ and NaBArf (0.109 g, 0.123 mmol) was added. The mixture was sonicated for a few seconds and the solution became bright orange as a faint white precipitate of NaCl developed. The mixture was filtered and the orange filtrate was loaded onto a silica gel column. The adsorbed orange band was washed with $CH_2Cl_2$ (100 mL) then eluted with $CH_2Cl_2$:MeOH 98.5/1.5. Two orange bands separated. The fast moving minor band was Λ-1. The slower moving major band was collected and concentrated by rotary evaporation to a bright orange solid which was further dried under oil pump vacuum at room temperature for 15 hours to yield Δ-1 (0.108 g).

1H NMR ($CD_2Cl_2$, 500 MHz) δ 7.72 (s, o-CH BArf-, 8H), 7.55 (s, p-CH BArf-, 4H), 7.34-7.28 (m, o-, m-, p-dpen, 30 H), 6.14 (br s, NH), 5.75 (br s, NH), 4.30 (s, CH, dpen, 6H), 2.48 (br s $H_2O$ and HDO, 11 H) 13C NMR ($CD_2Cl_2$, 125 MHz) 13C NMR ($CD_2Cl_2$, 125 MHz) for BArf-δ 161.7 (q, 1JBC=49.5 Hz, i), 134.7 (s, o), 128.8 (q, 2JCF=28.4 Hz, m), 124.5 (q, 1JCF=270.9 Hz, CF3), 117.4 (s, p), for dpen 134.0 (s), 129.9 (s), 129.3 (s), 127.3 (s), 65.8 (t, 2JCD=14.5 Hz, PhCHND$_2$).

EXAMPLE 5

Examples of Comparison of Z Counteranions

1H NMR spectra of cobalt complexes in $CD_2Cl_2$ after BArf-metathesis was obtained. Strong hydrogen bonding between one diastereotopic set of N—H bonds and Cl⁻ may be shown by a large downfield shift in 1H NMR spectra. In comparison with Cl⁻¹ weak hydrogen bond accepting anions such as triflate or tetraflouroborate leads to an upfield shift for these N—H bonds.

EXAMPLE 6

Procedures for Reactions Catalyzed Using Complexes

Figure 6A:
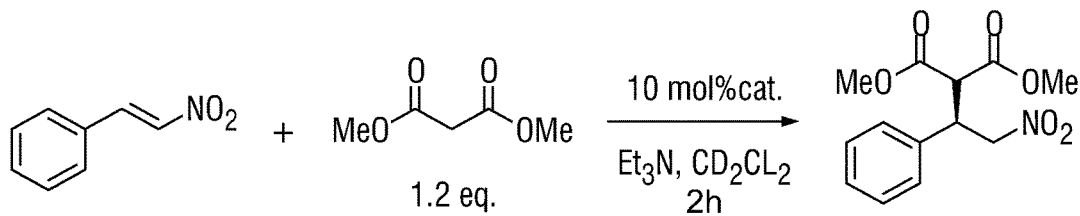
FIGS. 6A-6B show an illustrative carbon-carbon bond forming reaction to form enantiomer catalyzed by the Type 1 transition metal complexes disclosed herein, where
Figure 6B:
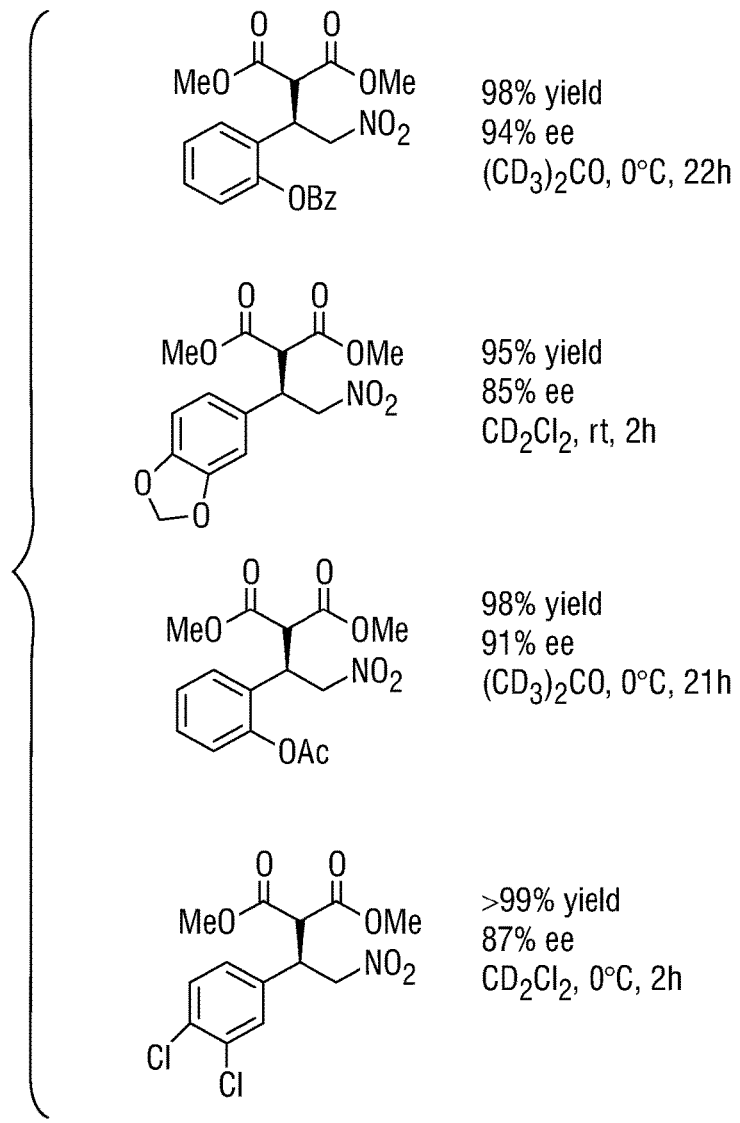
Figure 7:
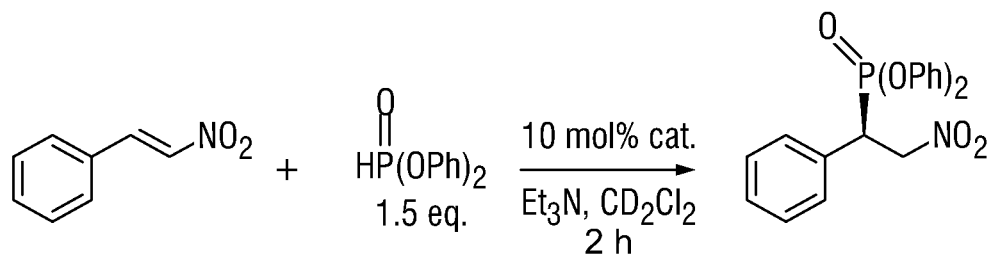
FIG. 7 shows an illustrative carbon-heteroatom bond forming reaction catalyzed by the catalysts obtained by procedure 2 described herein.

Referring to FIGS. 6A-6B and FIG. 7, the catalysts were used in illustrative bond forming reactions. Referring to FIGS. 6A-6B and FIG. 7, the chirality of the metal center determines the major product enantiomer in each illustrative reaction. FIGS. 6A-6B show an illustrative carbon-carbon bond forming reaction. FIG. 7 shows an illustrative carbon-heteroatom bond forming reaction.

The following three procedures are representative of how the catalysts are used in a reaction. The main difference in the procedures 1a and 1b is the solvent and base used in the reaction; however the reactants are the same. For procedure 2, the reactant has changed from dimethylmalonate to diphenylphosphite. In any of these procedures, the exact catalyst can be interchanged without any change in the reaction procedure. (For instance, in procedure 1, the Λ catalyst is used, but could just as easily have used the Δ catalyst. Procedure 1 was used to generate the results shown in FIG. 6A. Procedure 1b was used to generate the results shown in FIG. 6B. Procedure 2 was used to generate the results shown in FIG. 7.

General Procedure 1

An NMR tube was charged with a solution of trans-β-nitrostyrene (0.0054 g, 0.036 mmol), dimethylmalonate (0.0045 mL, 0.043 mmol), Λ-[Co(dpen)3](BArf)Cl2 (0.0050 g, 0.0036 mmol), and cyclohexane (0.0025 mL) in $CD_2Cl_2$ (0.4 mL). A 1H NMR of the bright orange solution was observed for a time=0 measurement. Then triethylamine (0.0045 mL, 0.036 mmol) was added to the NMR tube and the reaction proceeded at room temperature. Reaction conversion was monitored by 1H NMR until >99% conversion was achieved (2 h). The reaction solution was diluted with $CH_2Cl_2$ (1 mL) and passed through a short plug of silica with 1:1 EtOAc/hexanes (50 mL). The solvent was removed from the eluate by rotary evaporation and the resulting residue was analyzed by chiral HPLC to determine the enantiopurity of the desired product. (2 hours, >99% conversion, 80% ee R).

An NMR tube was charged with a solution of trans-β-nitrostyrene (0.0054 g, 0.036 mmol), dimethylmalonate (0.0045 mL, 0.043 mmol), Δ-[Co(dpen)3](BArf)Cl2 (0.0050 g, 0.0036 mmol), and cyclohexane (0.0025 mL) in $CD_2Cl_2$ (0.4 mL). A 1H NMR of the bright orange solution was observed for a time=0 measurement. Then triethylamine (0.0045 mL, 0.036 mmol) was added to the NMR tube and the reaction proceeded at room temperature. Reaction conversion was monitored by 1H NMR until >99% conversion was achieved (2 h). The reaction solution was diluted with $CH_2Cl_2$ (1 mL) and passed through a short plug of silica with 1:1 EtOAc/hexanes (50 mL). The solvent was removed from elute by rotary evaporation and the resulting residue was analyzed by chiral HPLC to determine the enantiopurity of the desired product. (2 hours, >99% conversion, 76% ee S).

General Procedure 1b

A vial is charged with a solution of trans-β-nitrostyrene (0.0054 g, 0.036 mmol), dimethylmalonate (0.0045 mL, 0.043 mmol), Λ-[Co(dpen)3](BArf)Cl2 (0.0050 g, 0.0036 mmol), and hexadecane (0.0025 mL) in $CH_2Cl_2$ (0.4 mL). An aliquot is removed from the mixture for a time=0 GC measurement. The bright orange solution is cooled to 0° C. and a solution of Na2CO3 (0.00038 g, 0.0036 mmol) in $H_2O$ (0.15 mL) is added. The biphasic mixture is stirred at 0° C. for 12 hours and the conversion is measured by analyzing a removed aliquot by GC. The reaction solution was diluted with $CH_2Cl_2$ (1 mL) and passed through a short plug of silica with 1:1 EtOAc/hexanes (50 mL). The solvent was removed from the eluate by rotary evaporation and the resulting residue was analyzed by chiral HPLC to determine the enantiopurity of the desired product. (12 hours, >95% conversion, 90% ee R).

A vial is charged with a solution of trans-β-nitrostyrene (0.0054 g, 0.036 mmol), dimethylmalonate (0.0045 mL, 0.043 mmol), Δ-[Co(dpen)3](BArf)Cl₂ (0.0050 g, 0.0036 mmol), and hexadecane (0.0025 mL) in $CH_2Cl_2$ (0.4 mL). An aliquot is removed from the mixture for a time=0 GC measurement. The bright orange solution is cooled to 0° C. and a solution of $Na_2CO_3$ (0.00038 g, 0.0036 mmol) in $H_2O$ (0.15 mL) is added. The biphasic mixture is stirred at 0° C. for 12 hours and the conversion is measured by analyzing a removed aliquot by GC. The reaction solution was diluted with $CH_2Cl_2$ (1 mL) and passed through a short plug of silica with 1:1 EtOAc/hexanes (50 mL). The solvent was removed from the eluate by rotary evaporation and the resulting residue was analyzed by chiral HPLC to determine the enantiopurity of the desired product. (12 hours, >99% conversion, 76% ee S).

General Procedure 2

An NMR tube is charged with a solution of trans-β-nitrostyrene (0.0054 g, 0.036 mmol), diphenylphosphite (0.0086 mL, 0.045 mmol), Δ-[Co(dpen)3](BArf)Cl₂ (0.0050 g, 0.0036 mmol), and cyclohexane (0.0025 mL) in $CD_2Cl_2$ (0.4 mL). A 1H NMR of the bright orange solution was observed for a time=0 measurement. Then triethylamine (0.0045 mL, 0.036 mmol) was added to the NMR tube and the reaction proceeded at room temperature. Reaction conversion was monitored by 1H NMR until full conversion was achieved (2 h). The reaction solution was diluted with $CH_2Cl_2$ (1 mL) and passed through a short plug of silica with 1:1 EtOAc/hexanes (50 mL). The solvent was removed from the eluate by rotary evaporation and the resulting residue was analyzed by chiral HPLC to determine the enantiopurity of the desired product. (1 hour, >99% conversion, 73% ee S).

An NMR tube is charged with a solution of trans-β-nitrostyrene (0.0054 g, 0.036 mmol), diphenylphosphite (0.0086 mL, 0.045 mmol), Λ-[Co(dpen)3](BArf)Cl₂ (0.0050 g, 0.0036 mmol), and cyclohexane (0.0025 mL) in $CD_2Cl_2$ (0.4 mL). A 1H NMR of the bright orange solution was observed for a time=0 measurement. Then triethylamine (0.0045 mL, 0.036 mmol) was added to the NMR tube and the reaction proceeded at room temperature. Reaction conversion was monitored by 1H NMR until full conversion was achieved (2 h). The reaction solution was diluted with $CH_2Cl_2$ (1 mL) and passed through a short plug of silica with 1:1 EtOAc/hexanes (50 mL). The solvent was removed from the eluate by rotary evaporation and the resulting residue was analyzed by chiral HPLC to determine the enantiopurity of the desired product. (1 hour, >99% conversion, 68% ee R).

EXAMPLE 7

Type 2 Transition Metal Complexes
Synthesis of Ligands

Different chiral ethylenediamine derivatives having different numbers of carbon atoms (n=2, 3) in the basic arms have been synthesized. Also, the ligand (n=3) with cycloalkylamine as Lewis base was also synthesized. The synthetic schemes are shown in the following.

Figure 16:
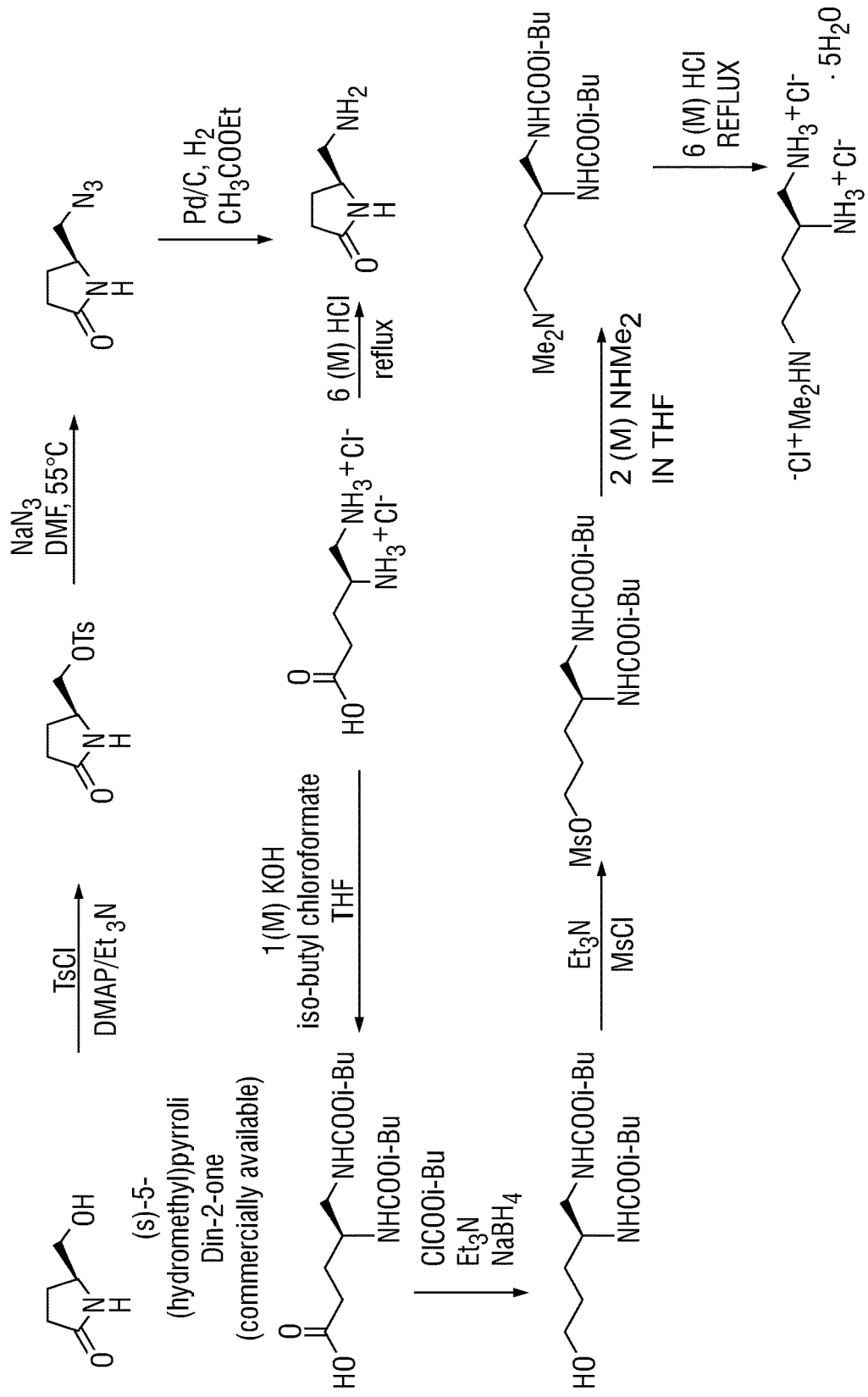
FIG. 16 shows synthesis of the salt of the ligand (S)-$N^5$,$N^5$-dimethylpentane-1,2,5-triamine (n=3)

Referring to FIG. 16, synthesis of the salt of the ligand (S)-N5,N5-dimethylpentane-1,2,5-triamine (n=3) is illustrated.

Figure 17:
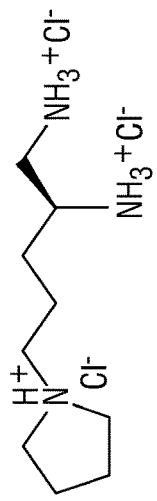
FIG. 17 shows the hydrochloric acid salt of the (S)-5-(pyrrolidin-1-yl)pentane-1,2-diamine.

Referring to FIG. 17, the hydrochloric acid salt of the (S)-5-(pyrrolidin-1-yl)pentane-1,2-diamine is illustrated. This salt of the ligand may be synthesized according to scheme 1 substituting dimethylamine by pyrrolidine during amination.

Figure 18:
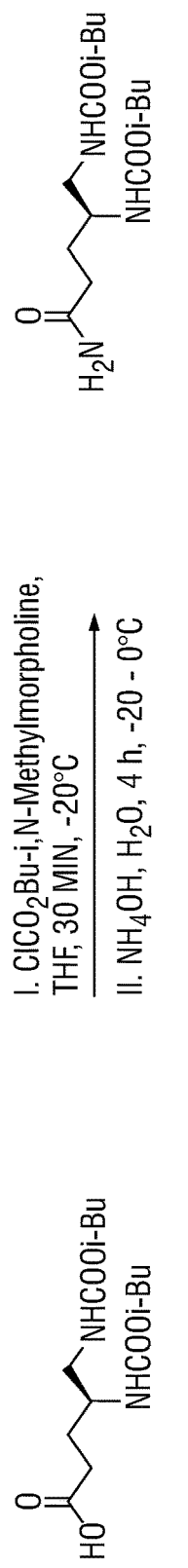
FIG. 18 shows the synthesis of the hydrochloric acid salt of (S)-$N^4$,$N^4$-dimethylbutane-1,2,4-triamine (n=2)
Figure 18:
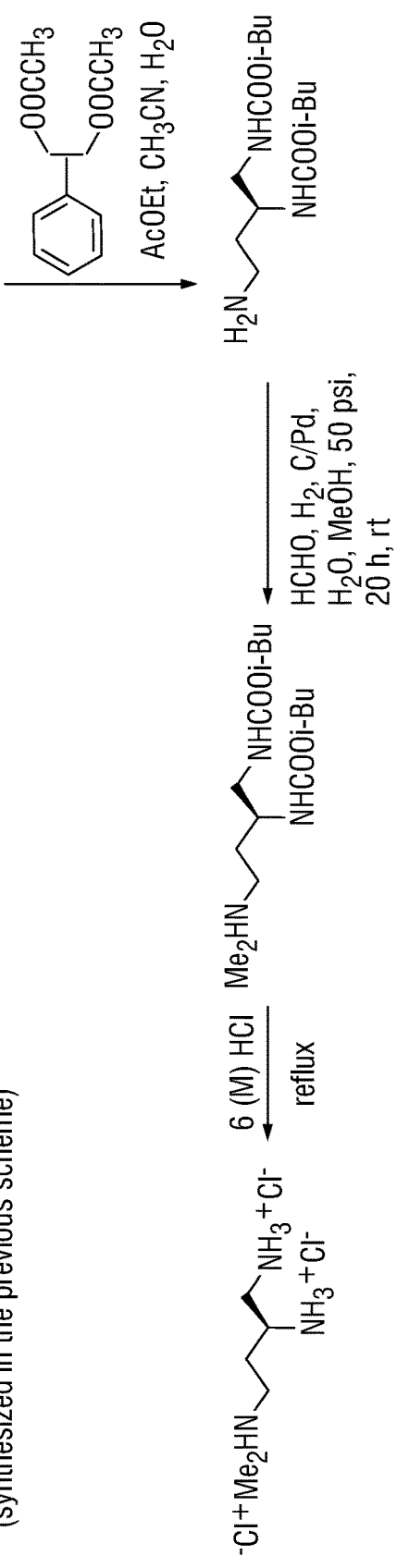

Referring to FIG. 18, the synthesis of the hydrochloric acid salt of (S)-N4,N4-dimethylbutane-1,2,4-triamine (n=2) is illustrated.

The procedures for the synthesis of ligands were adapted from Ghosh, A. K.; Leshchenko-Yashchuk, S.; Anderson, D. D.; Baldridge, A.; Noetzel, M.; Miller, H. B.; Tie, Y. F.; Wang, Y.-F.; Koh, Y.; Weber, I. T.; Mitsuya, H. J. Med. Chem. 2009, 52, 3902; Altman, J.; Ben-Ishai, D. Tetrahedron: Asymmetry 1993, 4, 91; and Ganzmann, C. Doctorate Thesis, Universitat Erlangen-NUrnberg, 2010.

EXAMPLE 8

Synthesis of the hydrochloric acid salt of (S)-N5,N5-dimethylpentane-1,2,5-triamine (n=3)

(a) (S)-(5-oxopyrrolidin-2-yl)methyl-4-methylbenzenesulfonate 1

A round bottom flask was charged with (S)-5-(hydroxymethyl)-2-pyrrolidinone (9.5 g, 82.6 mmol), p-toluenesulfonyl chloride (19.0 g, 100 mmol), and $CH_2Cl_2$ (200 mL), and cooled to 0° C. DMAP (2.12 g, 17.34 mmol) and $Et_3N$ (14 mL, 100.6 mmol) were added to the reaction mixture. The resulting mixture was allowed to warm to room temperature and stirred for overnight. The reaction was then quenched with 150 mL of water, and the aqueous layer was extracted with $CH_2Cl_2$. The combined organic extracts were washed with 1 N HCl and dried over anhydrous $Na_2SO_4$. Removal of solvent under reduced pressure followed by flash chromatography purification (100% EtOAc as the eluent) yielded (S)-(5-oxopyrrolidin-2-yl) methyl-4-methylbenzenesulfonate (18.43 g, 68.5 mmol, 79%) as a white solid.

1 H NMR (500 MHz, CDCl3, $\delta$ in ppm): 1.72-1.79 (m, 1 H), 2.19-2.31 (m, 3H), 2.44 (s, 3H), 3.85-3.92 (m, 2H), 4.02-3.99 (m, 1H), 6.53 (s, 1H), 7.35 (d, 2H, J=5.0 Hz), 7.77 (d, 2H, J=10 Hz); 13C NMR (125 MHz, CDCl3, $\delta$ in ppm): 21.6, 22.7, 29.2, 52.6, 71.9, 121.9, 127.8, 127.6, 130.0, 132.3, 145.3, 117.9.

(b) (S)-5-(azidomethyl) pyrrolidin-2-one1

A round bottom flask was charged with (S)-(5-oxopyrrolidin-2-yl)methyl-4-methylbenzenesulfonate (18.4 g, 68.5 mmol), DMF (400 mL), and $NaN_3$ (17.8 g, 274 mmol). The resulting mixture was stirred at 55° C. for overnight. Removal of solvent under reduced pressure followed by flash chromatography purification (7% MeOH in CHCl3 as the eluent) provided the (S)-5-(azidomethyl) pyrrolidin-2-one (8.45 g, 60.36 mmol, 88%) as a yellow oil.

1H NMR (500 MHz, $CDCl_3$, $\delta$ in ppm): 1.78-1.83 (m, 1H), 2.21-2.39 (m, 3H), 3.27-3.31 (dd, 1H, J=5 Hz, 15 Hz), 3.43-3.47 (dd, 1H, J=5 Hz, 15 Hz), 3.78-3.83 (m, 1H), 7.00 (s, 1H); 13C NMR (125.6 MHz, $CDCl_3$, $\delta$ in ppm): 24.0, 29.7, 53.5, 55.9, 178.4.

(c) (S)-5-(aminomethyl) pyrrolidin-2-one1

A round bottom flask was charged with the (S)-5-(azidomethyl) pyrrolidin-2-one (8 g, 57.14 mmol), EtOAc (400 mL). Pd/C (750 mg) was added to the reaction mixture. The mixture was stirred at room temperature under a hydrogen filled balloon for overnight, then filtered over Celite, and washed with EtOAc and MeOH. Removal of solvent under reduced pressure followed by flash chromatography purification (15% MeOH in CHCl3 as the eluent) afforded the corresponding (S)-5-(aminomethyl) pyrrolidin-2-one (4.9 g, 42.98 mmol, 75%) as a yellow oil.

1H NMR (500 MHz, $CDCl_3$, $\delta$ in ppm): 1.87 (br s, 2H), 1.62-1.68 (m, 1H), 2.07-2.13 (m, 1H), 2.21-2.27 (m, 2H), 2.60-2.56 (dd, 1H, J=5 Hz, 15 Hz), 2.74-2.78 (dd, 1H, J=5 Hz, 15 Hz), 3.57-3.62 (m, 1H), 7.79 (br s, 1H). 13C NMR (125.6 MHz, $CDCl_3$, $\delta$ in ppm): 24.4, 30.1, 47.8, 56.7, 179.0.

(d) (S)-4-carboxybutane-1,2-diaminium chloride2

A round bottom flask was charged with (S)-5-(aminomethyl)pyrrolidin-2-one (9.0 g, 79 mmol) and 400 mL of 6M HCl. The reaction mixture was heated to reflux for 20 h. The solvent was evaporated to dryness and the resulting solid was washed with MeOH-diethyl ether. Then the white solid was dried in vacuum to yield (S)-4-carboxybutane-1, 2-diaminium chloride (15.75 g, 76.8 mmol, 97%).

1H NMR (500 MHz, $D_2O$, $\delta$ in ppm): 1.83-1.99 (m, 2H); 2.48-2.45 (t, 2H); 3.20-3.19 (d, 2H); 3.59-3.53 (m, 1H); 13C NMR (125.6 MHz, $D_2O$, $\delta$ in ppm): 27.7, 31.9, 43.3, 51.5, 178.9

(e) (S)-4,5-bis((isobutoxycarbonyl)amino)pentanoic acid2

A round bottom flask was charged with (S)-4-carboxybutane-1,2-diaminium chloride (9.5 g, 46 mmol) and water (45 mL). The solution was neutralized with 1M KOH (145 mL) and cooled in an ice-bath. Simultaneously, from two separate additional funnels, isobutyryl chloroformate (13.3 mL) in THF (190 mL) and 1M KOH (145 mL) were slowly added. The mixture was stirred for 1 h at 0° C. and overnight at room temperature. THF was removed in vacuum and the water layer was extracted with EtOAc. The water layer was acidified with 2M HCl and extracted with EtOAc. The combined extract was dried over anhydrous $Na_2SO_4$. Removal of solvent under reduced pressure, gave 15.03 g (45.3 mmol, 98%) of (S)-4,5-bis((isobutoxycarbonyl) amino)pentanoic acid as white solid.

1H NMR (500 MHz, $CDCl_3$, $\delta$ in ppm): 0.88-0.89 (d, 12H); 1.74-1.89 (m, 4H); 2.42-2.57 (m, 2H), 3.28 (m, 2H), 3.74-3.81 (m, 5H), 5.22-5.30 (br, 2H).

(f) (S)-diisobutyl (5-hydroxypentane-1,2-diyl)dicarbamate3

A round bottom flask was charged with crude S)-4,5-bis ((isobutoxycarbonyl)amino)pentanoic acid (14.22 g, 42.84 mmol) and 1,2-dimethoxyethane (70 mL). N-methyl morpholine (5.24 mL, 47.1 mmol) was added with stirring and the resulting solution was cooled to −25° C. Then isobutyl chloroformate (6.8 mL, 51.4 mmol) was added slowly and a white precipitate formed. The cold bath was removed, and the mixture was allowed to warm to room temperature. The precipitate was collected by filtration and washed with 1,2-dimethoxyethane (2×30 mL). The combined filtrate and washings were deoxygenated with a stream of nitrogen, and a solution of $NaBH_4$ (2.43 g, 64.3 mmol) in EtOH (150 mL) was added dropwise at 0° C. After 2 h, water (10 mL) was cautiously added. The mixture was stirred overnight and the 0° C. bath was allowed to warm to room temperature. The solvent was removed by rotary evaporation. The resulting solid was dissolved in EtOAc (300 mL) and water (200 mL) was added. The aqueous phase was extracted with EtOAc (2×100 mL) and the combined organic phases were dried on anhydrous $Na_2SO_4$. The solvent was removed by rotary evaporation and the crude product was purified on a silica gel column (1:1 v/v EtOAc/Hexane). The solvent was removed and dried in vacuum to give (S)-diisobutyl (5-hydroxypentane-1,2-diyl)dicarbamate as a white solid (11.13 g, 35 mmol, 82%).

1H NMR (500 MHz, CDCl$_3$, δ in ppm): 5.17 (br s, 1H), 5.06 (br s, 1H), 3.90-3.76 (m, 4H), 3.75-3.59 (t, 3H), 3.36-3.18 (m, 2H), 1.97-1.81 (m, 2H), 1.69-1.56 (m, 3H), 1.55-1.43 (m, 1H), 0.97-0.86 (m, 12H). 13C NMR (125.6 MHz, CDCl$_3$, δ in ppm): 157.6, 157.3, 71.1, 62.4, 51.7, 45.1, 29.2, 28.6, 28.0, 19.0.

(g) (S)-4,5-bis((isobutoxycarbonyl)amino)pentyl methanesulfonate3

A round bottom flask was charged with (S)-diisobutyl (5-hydroxypentane-1,2-diyl)dicarbamate (5.0 g, 15.7 mmol), CH$_2$Cl$_2$ (80 mL), and triethylamine (5.3 mL, 38 mmol), and cooled to 78° C. Methanesulfonyl chloride (2.3 mL, 30 mmol) was added dropwise with stirring and the cold bath was allowed to warm to 0° C. over the course of 5 h. Aqueous citric acid (20%, 140 mL) and CH$_2$Cl$_2$ (150 mL) were added and the phases were separated. The organic phase was washed with saturated NaHCO$_3$ solution, and then dried on anhydrous Na$_2$SO$_4$. The solvent was removed by rotary evaporation and dried in oil pump vacuum. The product (S)-4,5-bis((isobutoxycarbonyl)amino)pentyl methanesulfonate was obtained as a yellowish white solid. The crude product was used without further purification in the next procedure.

(h) (S)-diisobutyl-(5-(dimethylamino)pentane-1,2-diyl)dicarbamate3

An airfree round bottom flask was charged with the crude (S)-4,5-bis((isobutoxycarbonyl)amino)pentyl methanesulfonate from the previous synthesis and a solution of HNMe$_2$ in THF (80 mL, 2.0 M). Then the stopper of the flask was tightened to stop the evaporation of HNMe$_2$ during the reaction. The mixture was placed in an 80° C. oil bath. After 15 h, the reaction mixture was cooled to room temperature and the solvent was removed by rotary evaporation. The residue was dissolved in CH$_2$Cl$_2$ (200 mL), washed with saturated NaHCO$_3$ (150 mL) and brine (100 mL), and dried on anhydrous Na$_2$SO$_4$. The solvent was removed by rotary evaporation and the oily yellow residue was purified by a silica gel column (with CH$_2$Cl$_2$/MeOH). The solvent was removed from the product-containing fractions to give (S)-diisobutyl-(5-(dimethylamino) pentane-1,2-diyl) dicarbamate as an oily yellow residue (4.66 g, 13.55 mmol, 88% for two steps).

1H NMR (500 MHz, CDCl$_3$, δ in ppm): 5.71 (br s, 1H), 5.27 (br s, 1H), 3.90-3.75 (d, J=10 Hz, 4H), 3.70-3.58 (m, 1H), 3.33-3.08 (m, 2H), 2.30-2.23 (m, 2H), 2.20 (s, 6H), 1.96-1.79 (m, 2H), 1.62-1.38 (m, 4H), 0.97-0.82 (m, 12H). 13C NMR (125.6 MHz, CDCl3, δ in ppm): 157.4, 157.3, 71.0, 59.1, 51.5, 45.4, 45.2, 30.4, 28.0, 23.6, 19.0.

(i) Hydrochloric acid salt of (S)—N5,N5-dimethylpentane-1,2,5-triamine

A round bottom flask was charged with (S)-diisobutyl-(5-(dimethylamino)pentane-1,2-diyl)dicarbamate (4.2 g, 12.2 mmol) and 6.0 M HCl (250 mL), and the solution was refluxed for 36 h. The acidic solvent was evaporated in vacuum and the hydrochloride salt of (S)-N5,N5-dimethylpentane-1,2,5-triamine was obtained as sticky solid with 71% yield (2.994 g, 8.7 mmol). The compound was highly hygroscopic.

1H NMR (500 MHz, D$_2$O, δ in ppm): 1.84-1.58 (m, 4H); 2.76 (s, 6H); 3.12-3.03 (m, 2H), 3.24-3.21 (m, 2H); 3.60-3.55 (m, 1H). 13C NMR (125.6 MHz, D2O, δ in ppm): 22.6, 29.6, 41.07, 43.1, 45.4, 51.6, 59.2.

EXAMPLE 9

Synthesis of hydrochloride salt of (S)-N4,N4-dimethylbutane-1,2,4-triamine (n=2)

(a) (S)-diisobutyl-(5-amino-5-oxopentane-1,2-diyl)dicarbamate

A round bottom flask was charged with (S)-4,5-bis((isobutoxycarbonyl)amino)pentanoic acid (4.0 g, 12 mmol) and anhydrous THF (130 mL). N-methyl morpholine (1.7 mL, 15.4 mmol) was added with stirring and the resulting solution was cooled to −20° C. Then isobutyl chloroformate (2.0 mL, 15.4 mmol) was added slowly and the mixture was stirred for 0.5 h. Conc. ammonium hydroxide (30%) (8.8 mL) was added and the mixture was stirred at −20° C. to 0° C. for 6 hours and then evaporated to dryness. The residue was purified by silica gel column chromatography using 7% (15% concentrated ammonium hydroxide in methanol)-CH$_2$Cl$_2$ as eluent. The solvent was removed and dried in vacuum to give (S)-diisobutyl-(5-amino-5-oxopentane-1,2-diyl) dicarbamate as a white solid (3.42 g, 10.2 mmol, 85%).

1H NMR (500 MHz, DMSO-d6, δ in ppm): 0.76-0.97 (m, 12H); 1.31-2.11 (m, 5H); 2.84-3.04 (m, 2H), 3.33 (s, 1H), 3.37-3.6 (m, 1H), 3.62-3.74 (m, 4H), 6.24-7.64 (br m, 4H). 13C{1H} NMR (125.6 MHz, DMSO-d6, δ in ppm): 174.0, 156.6, 156.2, 69.7, 69.4, 50.6, 44.2, 31.7, 27.7, 27.5, 19.0, 18.9.

(b) (S)-diisobutyl (4-aminobutane-1,2-diyl)dicarbamate4

A round bottom flask was charged with (S)-diisobutyl-(5-amino-5-oxopentane-1,2-diyl)dicarbamate (3.0 g, 9 mmol), CH$_3$CN (25 mL), EtOAc (25 mL), water (12 mL), and iodosobenzene diacetate (4.2 g, 13 mmol). The reaction mixture was stirred at room temperature. After 15 hours the solvents were evaporated and the crude mixture was purified by silica gel column chromatography (5% to 20% MeOH in CH$_2$Cl$_2$) to afford (S)-diisobutyl (4-aminobutane-1,2-diyl)dicarbamate as a colorless sticky liquid (1.55 g, 5.1 mmol, 57%).

1H NMR (500 MHz, CDCl$_3$, δ in ppm): 0.80-0.98 (d, 12H, J=5 Hz); 1.42-1.77 (m, 2H), 1.79-1.99 (m, 2H); 2.70-2.91 (m, 2H), 3.36-3.08 (br s, 2H), 3.82 (m, 5H), 5.2-5.60 (br, 2H). 13C NMR (125.6 MHz, CDCl$_3$, δ in ppm): 157.5, 157.3, 71.1, 50.0, 45.2, 38.4, 35.6, 28.0, 28.0, 19.0.

(c) (S)-diisobutyl (4-(dimethylamino)butane-1,2-diyl)dicarbamate

A fisher porter bottle was charged with (S)-diisobutyl (4-aminobutane-1,2-diyl)dicarbamate (1.8 g, 6 mmol), methanol (50 mL) and distilled water (15 mL) and 37% aqueous formaldehyde (1.6 mL). The mixture was stirred for 1 h and 10% wet Pd—C(1.2 g) was added in portions and the mixture was hydrogenated at 50 psi for 24 h at RT. The mixture was filtered through a plug of Celite and washed with methanol-distilled water (1:1). The solvent was removed and the residue was chromatographed on a silica gel column (5% to 20% methanol in CH$_2$Cl$_2$ to give (S)-diisobutyl (4-(dimethylamino)butane-1,2-diyl)dicarbamate (1.016 g, 51%) as colorless oil.

1H NMR (500 MHz, CDCl$_3$, δ in ppm): 0.80-1.02 (m, 12H), 1.52-1.99 (m, 4H), 2.14-2.41 (m, 6H); 2.41-2.66 (m, 2H), 3.13-3.38 (m, 2H), 3.66-3.94 (m, 5H), 5.36-6.12 (br, 2H). 13C NMR (125.6 MHz, CDCl$_3$, δ in ppm): 157.7, 157.4, 72.1, 71.2, 71.1, 50.9, 50.7, 45.0, 29.2, 28.0, 28.0, 19.9.

(d) Hydrochloride salt of (S)-N4,N4-dimethylbutane-1,2,4-triamine

A round bottom flask was charged with (S)-diisobutyl (4-(dimethylamino)butane-1,2-diyl)dicarbamate (0.9 g, 2.7 mmol) and 6 M HCl (50 mL). The reaction mixture was refluxed for 50 h. The acidic solvent was evaporated in vacuum and the hydrochloride salt (S)—N4,N4-dimethylbutane-1,2,4-triamine was obtained as sticky solid (0.607 g). The compound was highly hygroscopic.

1H NMR (500 MHz, $D_2O$, δ in ppm): 2.39-2.18 (m, 4H); 2.96 (s, 6H), 3.51-3.33 (m, 2H), 3.86-3.75 (m, 1H). 13C NMR (125.6 MHz, $D_2O$, δ in ppm): 26.3, 41.2, 43.6, 47.8, 53.8.

Hydrochloride salt of (S)-5-(pyrrolidin-1-yl)pentane-1,2-diamine (n=3)

(S)-diisobutyl-(5-(pyrrolidin-1-yl)pentane-1,2-diyl)dicarbamate.

An air free round bottom flask was charged with the previously synthesized crude (S)-4,5-bis((isobutoxycarbonyl)amino)pentyl methanesulfonate (1.79 g, 4.52 mmol) and THF (15 mL). Pyrrolidine (3.7 mL, 45.2 mmol) was added to the reaction mixture. Then the stopper of the flask was tightly closed. The mixture was placed in an 80° C. oil bath. After 15 h, the reaction mixture was cooled to room temperature and the solvent was removed by rotary evaporation. The residue was dissolved in $CH_2Cl_2$ (40 mL), washed with saturated $NaHCO_3$ (30 mL) and brine (20 mL), and dried on anhydrous $Na_2SO_4$. The solvent was removed by rotary evaporation and the oily yellow residue was purified by a silica gel column (with $CH_2Cl_2$/MeOH). The solvent was removed from the product-containing fractions to give (S)-diisobutyl-(5-(pyrrolidin-1-yl)pentane-1,2-diyl)dicarbamate (1.45 g, 4.08 mmol, 90%).

1H NMR (500 MHz, $CDCl_3$, δ in ppm): 5.99 (br s, 1H), 5.27 (br s, 1H), 3.95-3.73 (d, J=10 Hz, 4H), 3.72-3.54 (m, 1H), 3.36-3.06 (m, 2H), 2.58-2.29 (m, 6H), 1.94-1.80 (m, 2H), 1.79-1.75 (m, 4H), 1.66-1.38 (m, 4H), 0.99-0.78 (d, J=15 Hz, 12H); 13C NMR (125.6 MHz, $CDCl_3$, δ in ppm): 157.6, 157.5, 71.2, 71.1, 56.1, 54.1, 51.4, 45.6, 30.9, 28.1, 24.9, 23.5, 19.2.

EXAMPLE 10

Hydrochloride salt of the (S)-5-(pyrrolidin-1-yl)pentane-1,2-diamine

A round bottom flask was charged with (S)-diisobutyl-(5-(pyrrolidin-1-yl)pentane-1,2-diyl)dicarbamate (1.44 g, 4.05 mmol) and 6.0 M HCl (70 mL), and the solution was refluxed for 30 h. The acidic solvent was evaporated in vacuum and the hydrochloride salt of (S)-5-(pyrrolidin-1-yl)pentane-1,2-diamine was obtained as yellowish sticky solid (1.30 g). The compound was highly hygroscopic. See FIG. 2b.15.

1H NMR (500 MHz, $D_2O$, δ in ppm): 3.77-3.62 (m, 3H); 3.44-3.32 (m, 2H); 3.31-3.21 (m, 2H), 2.24-2.08 (m, 2H); 2.06-1.73 (m, 6H); 13C NMR (125.6 MHz, $D_2O$, δ in ppm): 54.8, 54.4, 49.6, 41.1, 27.8, 23.2, 22.0.

EXAMPLE 11

Synthesis of Metal Complexes

Synthesis and purification of cobalt complexes were adapted from Ganzmann, C. Doctorate Thesis, Universitat Erlangen-NUrnberg, 2010.

$[Co(en)_2(S)\text{-en }CH_2CH_2NMe_2]^{3+}3$ Barf−

A round bottom flask was charged with $[Co(en)_2CO_3]^{3+}Cl^-$ (0.606 g, 2.21 mmol), activated charcoal (0.440 g), and water (20 mL), and fitted with a condenser. The reaction mixture was heated to 40° C. Then the hydrochloric acid salt of (S)-N5,N5-dimethylpentane-1,2,5-triamine (0.519 g, 2.04 mmol) was added in one portion. The temperature was increased to 100° C. After 0.8 h, the activated charcoal was removed by filtration and the red filtrate was evaporated to dryness by rotary evaporation. The red solid was dissolved in 0.5 M HCl (100 mL), and sorbed on a Dowex (50WX2 hydrogen form, 200-400 mesh) column (4.2×15 cm), which was eluted with 1.0 M (250 mL) followed by 2.0 M HCl solution. Three distinguishable orange bands were obtained. When the second orange band reached the column outlet, the eluent was changed to 3.0 M HCl. The second orange band was collected, and evaporated to dryness to give an orange solid (0.380 g).

Figure 19:
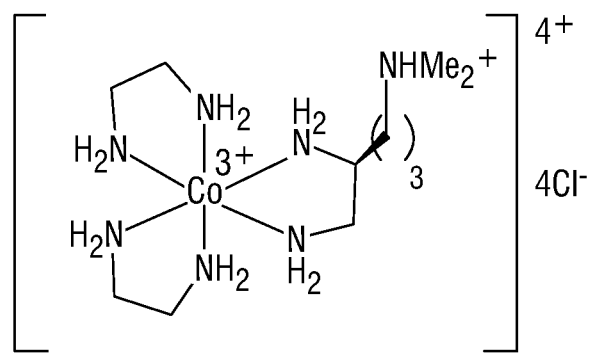
FIG. 19 shows the structure of the orange solid $[Co(en)_2(S)\text{-en}CH_2CH_2CH_2NMe2H]^{4+}4Cl^-$.

Referring to FIG. 19, the orange solid was $[Co(en)_2(S)\text{-}enCH_2CH_2CH_2NMe_2H]^{4+}4Cl^-$.

1H NMR (500 MHz, $D_2O$, δ in ppm): 5.4-4.85 (br m, 10H), 4.64-4.37 (br m, 2H) 3.27-3.13 (m, 2H), 3.12-2.69 (m, 16H), 2.66-2.59 (br s, 1H), 2.01-1.72 (br m, 4H); 13C{1H} NMR (125.6 MHz, $D_2O$, δ in ppm): 58.4, 57.6, 57.0, 49.6, 48.7, 45.6, 45.6, 45.5, 45.3, 45.3, 45.2, 45.0, 44.9, 43.2, 29.2, 29.0, 22.0 (Dioxane as ref. at 67.14 ppm).

The orange solid obtained from second band of the Dowex column was redissolved in 40 mL of water and sorbed in a SP Sephadex (C-25) column (4.4×44 cm). Two bands separated upon elution with 0.10 M (250 mL), 0.15 M (250 mL), 0.20 M (500 mL) and 0.25 M 2Na+d-tart2-.2H$_2$O.

The first band from the Sephadex column was collected and concentrated to 100 mL. This solution was sorbed on a Dowex column. Then, the compound was eluted by using 1 (M) to 3 (M) HCl solutions to give an orange solid (0.230 g).

Figure 20:
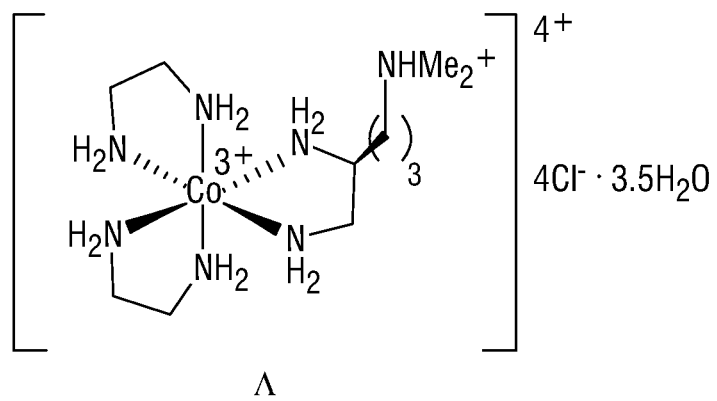
FIG. 20 shows the structure of the compound in the first fraction obtained from the Dowex column during the synthesis and purification of cobalt complexes (Fr-1 $[Co(en)_2(S)\text{-en}CH_2CH_2CH_2NMe2H]^{4+}4Cl^-.3.5H_2O$)

Referring to FIG. 20, the first band gave $(Co(en)_2(S)\text{-}enCH_2CH_2CH_2NMe_2H]^{4+}4Cl^-.3.5H_2O$. (Fr-1 $[Co(en)_2(S)\text{-}enCH_2CH_2CH_2NMe_2H]^{4+}4Cl^-.3.5H_2O$).

1H NMR (500 MHz, $D_2O$, δ in ppm): 5.5-4.84 (br m, 10H), 4.69-4.43 (br m, 2H) 3.26-3.13 (m, 2H), 3.11-2.69 (m, 18H), 2.66-2.49 (br s, 1H), 2.04-1.67 (br m, 4H). 13C{1H} NMR (125.6 MHz, $D_2O$, δ in ppm): 58.4, 57.6, 49.6, 45.5, 45.3, 45.3, 45.2, 43.2, 29.2, 29.0, 22.0. (Dioxane as ref. at 67.14 ppm).

Similarly, the second band from the Sephadex column was collected and concentrated to 100 mL. Then the solution was sorbed on a Dowex column. Then, the compound was eluted by using 1.0 (M) to 3.0 (M) HCl solutions to give an orange solid (0.134 g).

Figure 21:
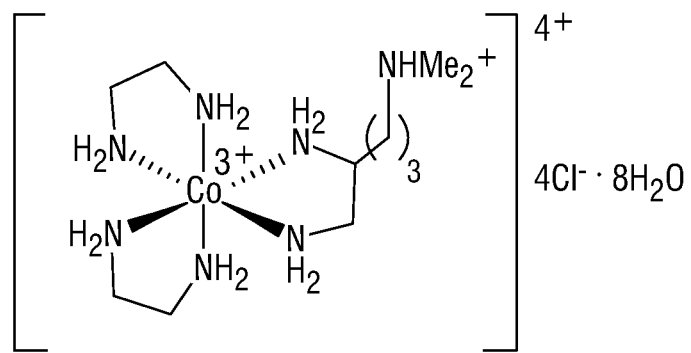
FIG. 21 shows the structure of $[Co(en)_2(S)\text{-en}CH_2CH_2CH_2NMe2H]^{4+}4Cl^-.8H_2O$)

Referring to FIG. 21, the second band gave Fraction-2-$[Co(en)_2(S)\text{-}enCH_2CH_2CH_2NMe_2H]^{4+}4Cl^-.8H2O$.

1H NMR (500 MHz, $D_2O$, δ in ppm): 5.4-5.26 (br s, 1H), 5.22-4.95 (br m, 5H), 4.64-4.35 (br 2H), 3.27-3.08 (m, 3H), 3.07-2.48 (m, 16H), 2.66-2.59 (br s, 1H), 1.98-1.68 (br m, 4H); 13C{1H} NMR (125.6 MHz, $D_2O$, δ in ppm): 58.4, 57.0, 48.7, 45.6, 45.0, 44.9, 43.3, 29.1, 22.0 (Dioxane as ref. at 67.14 ppm).

A round bottom flask was charged with Fraction 1-[Co(en)$_2$(S)-en $CH_2CH_2CH_2NHMe_2]^{4+}4Cl^-.3.5H_2O$ (0.070 g, 0.134 mmol), aq. NaOH (1.5 mL, 0.10 mmol), and water (10 mL). Then a solution of Na+ BArf-(0.335 g, 0.361 mmol) in $CH_2Cl_2$ (20 mL) was added and the heterogeneous mixture was vigorously stirred for 0.5 h. The orange organic phase was separated from the aqueous phase and washed with water and allowed to evaporate in the air to give Fraction-1 $[Co(en)_2(S)\text{-}en\ CH_2CH_2CH_2NMe_2]^{3+}3BArf-.6.5H_2O$ as an orange powder (0.318 g).

Figure 22:
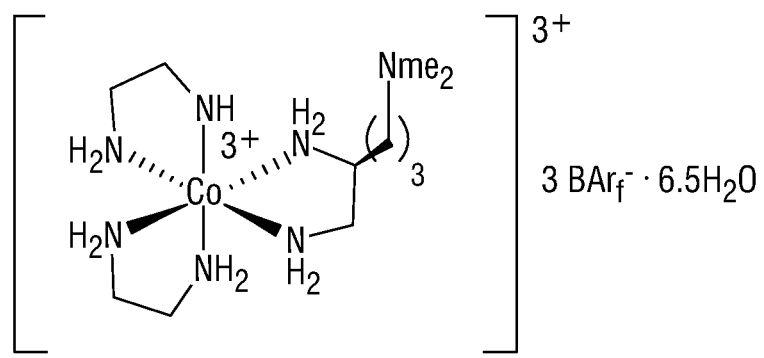
FIG. 22 shows the structure of $[Co(en)_2(S)\text{-en}CH_2CH_2CH_2NMe_2]^{3+}3BAr_f^-.6.5\ H_2O$.

Referring to FIG. 22, the orange powder is Fraction-1 $[Co(en)_2(S)\text{-}en\ CH_2CH_2CH_2NMe_2]^{3+}3BArf-.6.5H_2O$.

1H NMR (500 MHz, DMF-d7, δ in ppm): 7.91-7.69 (m, 35H), 5.56-4.98 (m, 10H), 4.73 (br s, 1H), 3.5 (s, 13H), 3.27 (br s, 1H), 3.15-2.93 (br s, 7H), 2.29-2.07 (m, 14H), 1.84-1.41 (m, 4H). 13C{1H} NMR (125.6 MHz, $CD_3CN$, δ in ppm): 162.6 (q, 1JBC=49.6 Hz), 135.7 (s), 129.9 (q, 2JCF=31.4 Hz), 125.5 (q, 1JCF=271.3 Hz), 118.7, 59.2, 50.1, 45.8, 45.6, 45.3, 45.3, 30.3, 24.6.

A round bottom flask was charged with Fraction-2 [Co(en)$_2$(S)-en CH$_2$CH$_2$CH$_2$NMe$_2$]$^{4+}$4Cl-.8H$_2$O (0.085 g, 0.143 mmol), aq. NaOH (1.5 mL, 0.1 M), and water (15 mL). Then a solution of Na+ BArf-(0.371 g) in CH$_2$Cl$_2$ (20 mL) was added and the heterogeneous mixture was vigorously stirred for 0.5 h. The orange organic phase was separated from the aqueous phase and the organic phase was washed with water and allowed to evaporate in the air to give Fraction-2 [Co(en)$^2$(S)-en CH$^2$CH$^2$CH$^2$NMe$^2$]$^{3+}$ 3BArf-.15H$_2$O as an orange powder.

Figure 23:
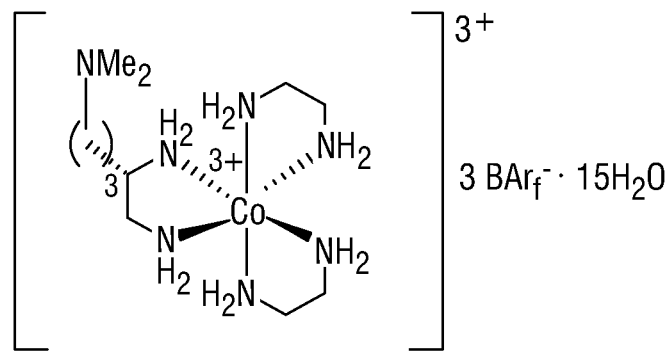
FIG. 23 shows the structure $[Co(en)_2(S)\text{-en}CH_2CH_2CH_2NMe_2]^{3+}3\ BAr_f^-.15H_2O$.

Referring to FIG. 23, the second orange powder is Fraction-2 [Co(en)$_2$(S)-en CH$_2$CH$_2$CH$_2$NMe$_2$]$^{3+}$3 BArf-.15H$_2$O.

1H NMR (500 MHz, DMF-d7, δ in ppm): 7.86-7.70 (m, 48H), 5.78-5.02 (m, 10H), 4.91-67 (br m, 2H), 3.51 (s, 30H), 3.36 (br s, 1H), 3.18-2.93 (br s, 9H), 2.4-1.95 (br s, 10H), 1.88-1.37 (m, 4H).

Co(en)$_2$(S)-en CH$_2$CH$_2$NMe$_2$]$^{3+}$3Barf–

A round bottom flask was charged with [Co(en)$_2$CO$_3$]$^{3+}$ Cl-(0.606 g, 2.21 mmol), activated charcoal (0.440 g), and water (20 mL), and fitted with a condenser. The reaction mixture was heated to 40° C. Then the hydrochloric acid salt of (S)-N4,N4-dimethylbutane-1,2,4-triamine (n=2) (0.494 g, 2.04 mmol) was added in one portion. The temperature was increased to 100° C. After 0.8 h, the activated charcoal was removed by filtration and the red filtrate was evaporated to dryness by rotary evaporation. The red solid was dissolved in 0.5 M HCl (100 mL), and sorbed on a Dowex (50WX2, 200-400 mesh) column (4.2×15 cm), which was eluted with 1.0 M (250 mL) followed by 2.0 M HCl. Three distinguishable orange bands were obtained. When the second orange band reached the column outlet, the eluent was changed to 3.0 M HCl. The second orange band was collected, and evaporated to dryness to give an orange solid (0.372 g).

Figure 24:
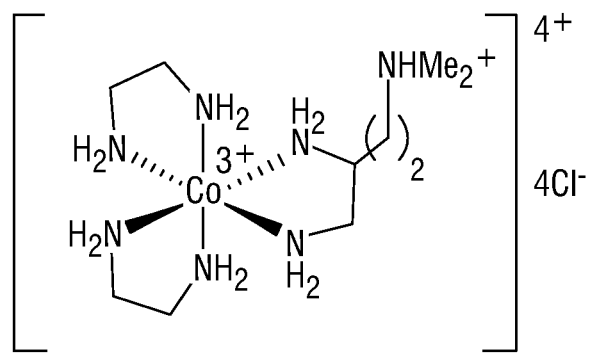
FIG. 24 shows the structure of $[Co(en)_2(S)\text{-en}CH_2CH_2NMe_2H]^{4+}4Cl^-$.

Referring to FIG. 24, the orange solid was [Co(en)$_2$(S)-enCH$_2$CH$_2$NMe$_2$H]4+4Cl-.

1H NMR (500 MHz, D$_2$O, δ in ppm): 5.6-4.82 (br m, 9H), 4.75-4.38 (m, 1H), 3.45-3.24 (m, 2H), 3.23-2.56 (m, 17H), 2.30-2.15 (m, 2H). 13C{1H} NMR (125.6 MHz, D$_2$O, δ in ppm): 56.0, 55.9, 55.0, 54.8, 54.7, 49.5, 48.6, 45.4, 45.3, 45.2, 45.1, 45.0, 43.5, 43.4, 43.3, 27.3.

The orange solid (0.300 g) obtained from second band of the Dowex column was redissolved in 40 ml of water and sorbed in a SP Sephadex (C-25) column (4.4×44 cm). Two bands separated upon elution with 0.10 M (1000 mL), 0.15 M (1000 mL), 0.20 M (1000 mL) and of 0.25 M 2Na+-d-tart2-.2H$_2$O. Each band was collected and concentrated.

The first band from the Sephadex column was collected and concentrated to 100 mL. This solution was sorbed on a Dowex column. Then, the compound was eluted by using 1.0 (M) to 3.0 (M) HCl solutions to give an orange solid (0.181 g).

Figure 25:
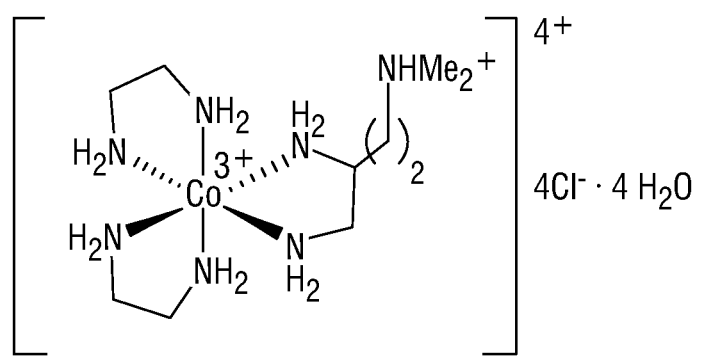
FIG. 25 shows the structure of $[Co(en)_2(S)\text{-en}CH_2CH_2NMe_2H]^{4+}4Cl^-.4H_2O$.

Referring to FIG. 25, the first band gave [Co(en)$_2$(S)-enCH$_2$CH$_2$NMe$_2$H]$^{4+}$4Cl-.4H$_2$O.

1H NMR (500 MHz, D$_2$O, δ in ppm): 5.46 (br s, 1H), 5.27-4.84 (br m, 11H), 3.46-3.23 (br m, 2H) 3.19-2.61 (m, 18H), 2.32-2.14 (m, 2H), 13C{1H} NMR (125.6 MHz, D$_2$O, δ in ppm): 55.76, 54.9, 49.2, 45.2, 45.1, 45.0, 44.9, 43.5, 43.3 (Dioxane as ref. at 67.14 ppm).

The second band from the Sephadex column was collected and concentrated to 100 mL. This solution was sorbed on a Dowex column. Then, the compound was eluted by using 1(M) to 3 (M) HCl solutions to give an orange solid (0.091 g).

Figure 26:
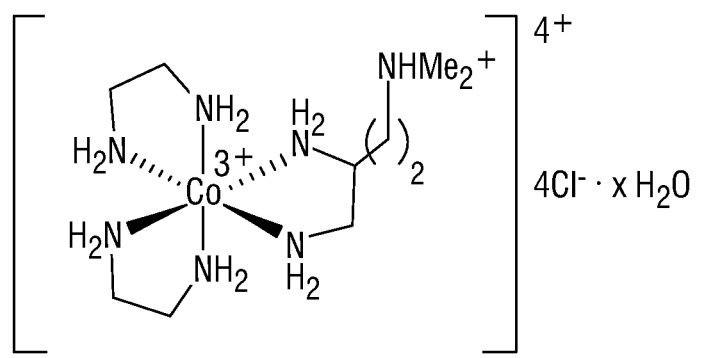
FIG. 26 shows the structure of $[Co(en)_2(S)\text{-en}CH_2CH_2NMe_2H]^{4+}4Cl^-.x\ H_2O$.

Referring to FIG. 26, the second band gave Fraction-2-[Co(en)$_2$(S)-enCH$_2$CH$_2$NMe$_2$H]$^{4+}$4Cl-.x H$_2$O.

1H NMR (500 MHz, D$_2$O, δ in ppm): 5.38 (br s, 1H), 5.27-5.05 (br m, 5H), 4.74-4.66 (br m, 1H), 4.58-4.48 (br m, 1H), 3.49-3.33 (br m, 2H), 3.32-3.20 (br m, 1H) 3.09-2.68 (m, 16H), 2.34-2.21 (m, 2H), 13C{1H} NMR (125.6 MHz, D$_2$O, δ in ppm): 55.0, 54.8, 48.6, 45.7, 45.6, 45.1, 45.0, 43.4, 43.3 (Dioxane as ref. at 67.14 ppm).

A round bottom flask was charged with Fr 1-[Co(en)$_2$(S)-en CH$_2$CH$_2$NHMe$_2$]$^{4+}$4 Cl-.4H$_2$O (0.051 g, 0.133 mmol), aq NaOH (1.5 mL, 0.1 M), and water (12 mL). Then a solution of Na+ BArf-(0.250 g) in CH$_2$Cl$_2$ (20 mL) was added and the heterogeneous mixture was vigorously stirred for 0.5 h. The orange organic phase was separated from the aqueous phase and the organic phase was washed with water and allowed to evaporate in the hood to give Fr-1 [Co(en)$_2$(S)-en CH$_2$CH$_2$NMe$_2$]$^{3+}$3 BArf-.12H$_2$O as an orange powder (0.302 g).

Figure 27:
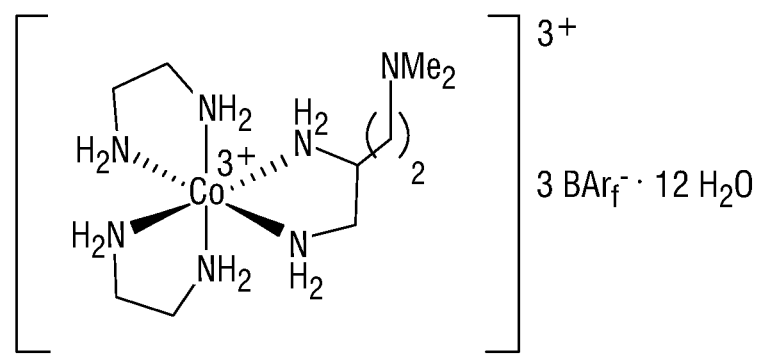
FIG. 27 shows the structure of $[Co(en)_2(S)\text{-en}CH_2CH_2NMe_2]^{3+}3BArf^-.12H_2O$.

Referring the FIG. 27, the orange powder was Fraction-1 [Co(en)$_2$(S)-en CH$_2$CH$_2$NMe$_2$]$^{3+}$3BArf-.12H$_2$O.

1H NMR (500 MHz, CD$_3$CN, δ in ppm): 7.76-7.58 (m, 35H), 4.56-3.53 (br m, 12H), 3.03-2.58 (br m, 10H), 2.56-2.44 (m, 2H), 2.40-2.29 (m, 1H), 2.27-2.21 (br s, 24H), 2.19 (s, 1H), 1.91-1.86 (m, 1H), 1.75-1.65 (m, 1H). 13C{1H} NMR (125.6 MHz, CD$_3$CN, δ in ppm): 162.6 (q, 1JBC=50.2 Hz), 135.7 (s), 129.9 (q, 2JCF=31.4 Hz), 125.5 (q, 1JCF=271.3 Hz), 118.7, 58.8, 56.7, 49.4, 45.7, 45.6, 45.3, 45.2, 28.2.

[Co((S)-enCH$_2$CH$_2$CH$_2$NMe$_2$H)$_3$]$^{6+}$6Cl_.

A round bottom flask was charged with a solution of CoCl$_2$.6H$_2$O (0.257 g, 1.08 mmol, 1 eq) in 2.5 mL water. Then the hydrochloric acid salt of (S)-N5,N5-dimethylpentane-1,2,5-triamine (1.45 g, 4.3 mmol, 4 eq) was added with stirring. The mixture was stirred for 15 min. NaOH (0.550 g, 12 eq) was added and the mixture was stirred until the NaOH dissolved completely. The solution becomes dark red. 3% H$_2$O$_2$ solution (1.6 mL) was added with stirring. The solution became dark upon addition of peroxide. The mixture was diluted to 6.0 mL and boiled for 0.5 h. Then, 3.0 M HCl (1 mL) was added with stirring. After cooling to room temperature, the reaction mixture was evaporated to dryness. The residue was dissolved in 1.0 (M) HCl (50 mL) and the mixture was sorbed on a Dowex column (4.2×15 cm), which was eluted with 1.0 M HCl (250 mL) followed by 2.0 M HCl (250 mL), 3.0 M HCl (250 mL) and 4.0 M HCl. The compound was collected by eluting with 4.0 M HCl and the orange to red colored solution was evaporated to dryness to give a deep red solid (0.994 g) which was the mixture of the diastereomers.

Figure 28:
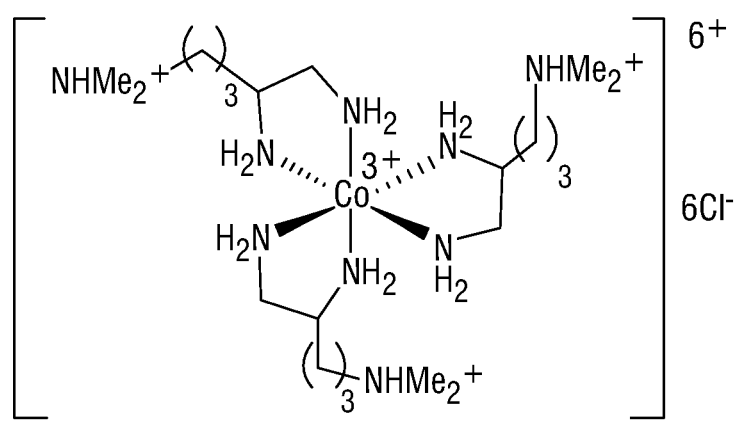
FIG. 28 shows the structure of $[Co((S)\text{-en}CH_2CH_2CH_2NMe_2H)_3]^{6+}6Cl^-$.

Referring to FIG. 28, the red solid was [Co((S)-enCH$_2$CH$_2$CH$_2$NMe$_2$H)3]$^{6+}$6 Cl-.

1H NMR (500 MHz, D$_2$O, δ in ppm): 5.47-4.86 (br m, 8H); 3.24-2.96 (br m, 12H), 2.87 (s, 18H), 2.68-2.53 (br m, 3H), 2.68-2.53 (br m, 12H); 13C{1H} NMR (125.6 MHz, D$_2$O, δ in ppm) 58.55/58.51/58.49/58.44, 57.57/57.54, 49.62/49.61, 43.33/43.28, 28.97/28.87/28.86/28.84, 21.99/21.97.

EXAMPLE 12

Procedures for Reactions Catalyzed Using Type 2 Transition Metal Complexes

The complexes Fraction-1 [Co(en)$_2$(S)-en CH$_2$CH$_2$CH$_2$NMe$_2$]$^{3+}$3 BArf-.6.5H$_2$O, Fr-2 [Co(en)2(S)-en CH$_2$CH$_2$CH$_2$NMe$_2$]$^{3+}$3BArf-.15H$_2$O, Fraction-1 [Co(en)$_2$ (S)-en CH$_2$CH$_2$NMe$_2$]$^{3+}$3 BArf-.12H$_2$O were tested as catalysts in the Michael addition of trans-β-nitrostyrene and diethyl malonate.

Figure 29:
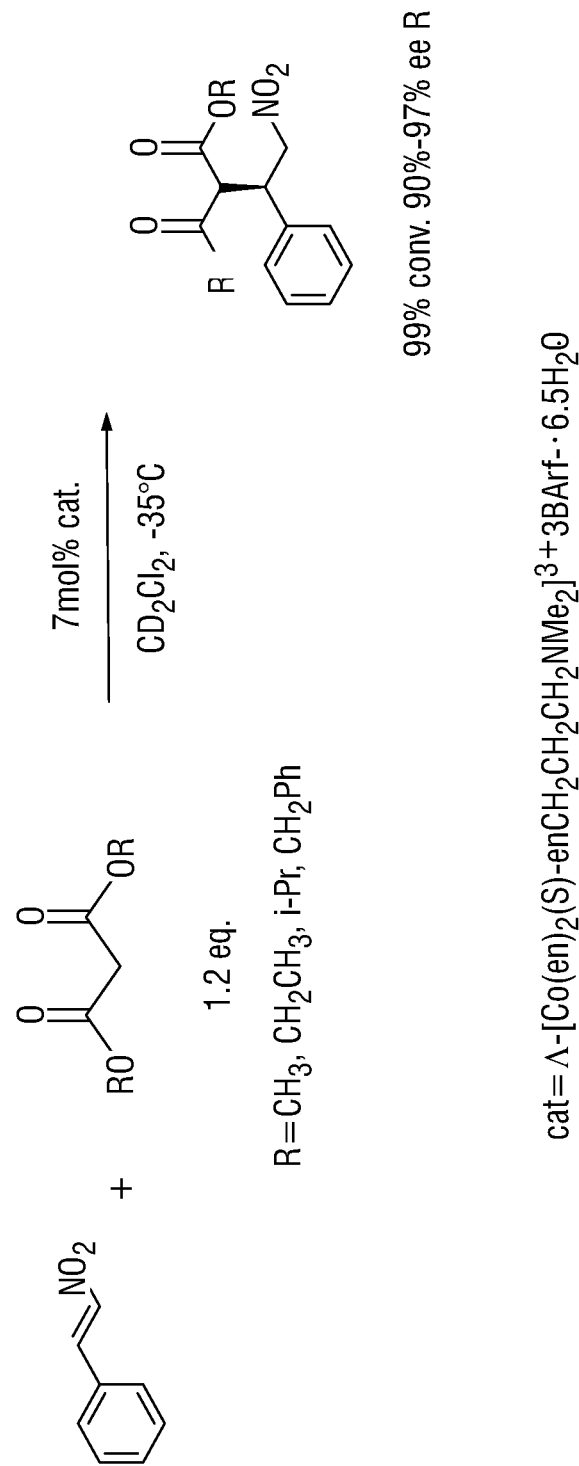
FIG. 29 shows the results of the catalyzed Michael addition of trans-$\beta$-nitrostyrene and diethyl malonate ranged from 76-85% R using Fr-1 $[Co(en)_2(S)\text{-en}CH_2CH_2CH_2NMe_2]^{3+}3\ BAr_f^-.6.5H_2O$.

Referring to FIG. 29, results the catalyzed Michael addition of trans-β-nitrostyrene and diethyl malonate ranged from 76-85% ee R using Fr-1 [Co(en)$_2$(S)-en CH$_2$CH$_2$CH$_2$NMe$_2$]$^{3+}$3 BArf-.6.5H$_2$O.

The complex Fraction-1 [Co(en)$_2$(S)-en CH$_2$CH$_2$CH$_2$NMe$_2$]$^{3+}$ 3BArf-.6.5H$_2$O was found to be the best catalyst, with higher yield and enantioselectivity, for the Michael addition of trans-β-nitrostyrene and diethyl malonate.

General Procedure for Michael Addition

A NMR tube was charged with β-nitrostyrene (0.0149 g, 0.10 mmol), diethyl malonate (0.0182 mL, 0.012 mmol), catalyst (7 mol %), 1,2-dichloroethane (0.0080 mL, 0.10 mmol) as internal standard, and CD$_2$Cl$_2$ (0.4 mL). The NMR tube was sealed with a plastic cap and parafilm. The reaction was monitored by 1H NMR. The reaction solution was passed through a short pad of silica with hexanes and ethyl acetate mixture. The solvent was evaporated by rotary evaporation. Then the enantioselectivity for the reactions were measured by chiral HPLC.

EXAMPLE 13

Type 3 Transition Metal Complexes
Synthesis of Metal Complexes

Figure 38:
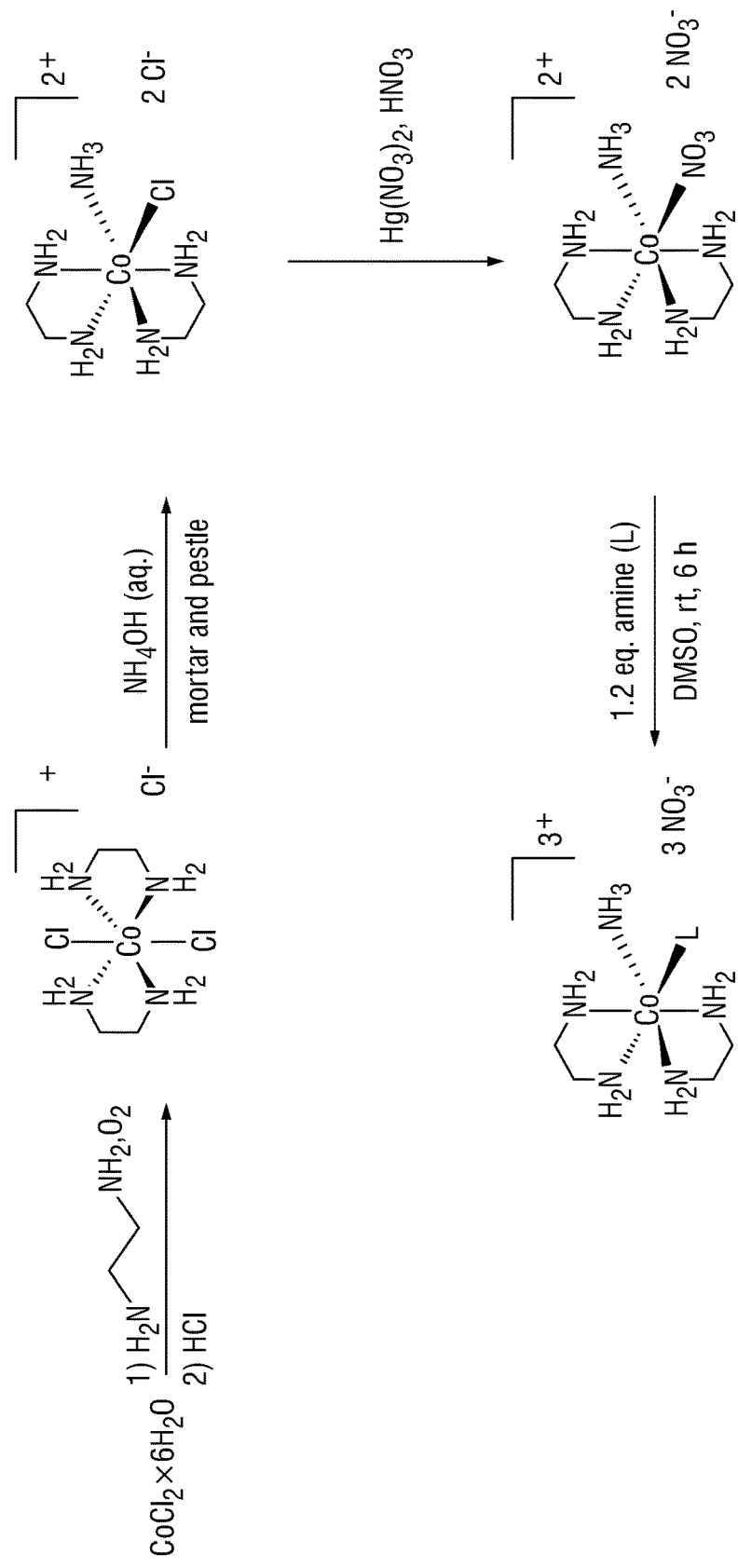
FIG. 38 shows a synthesis procedure for cobalt complexes having 1°/3° ligand (L)

Referring to FIG. 38, shown is a synthesis procedure for cobalt complexes having 1°/3° ligand (L).

Examples of Synthesis of Metal Complexes

The following experimental illustrates synthesis of cobalt complexes having 1°/3° ligand (L).

Figure 39:
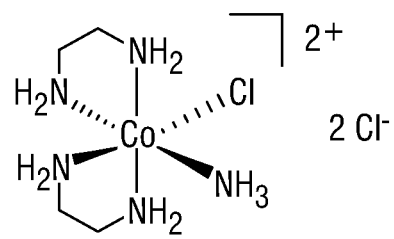
FIG. 39 shows the structure of cis-$[Co(en)_2(NH_3)Cl]Cl_2$ prepared by the procedure described in FIG. 38.

Referring to FIG. 39, cis-[Co(en)$_2$(NH$_3$)Cl]Cl$_2$ was prepared. A flame dried Schlenk flask was put under N$_2$ atmosphere and charged with trans-[Co(en)$_2$Cl$_2$]Cl (0.6635 g, 2.232 mmol) which was suspended in dry MeOH (30 mL). The stirring suspension was warmed to 55° C. and an ammonia solution (2.0 M in EtOH) (2.0 mL, 4.0 mmol) was added in a slow stream via syringe. The reaction mixture rapidly changes color from green to red. For a few moments after the addition, the reaction mixture becomes homogeneous. Immediately upon removing the reaction from the oil bath, a red precipitate begins to form. Returning the flask to the oil bath for 10 minutes did not dissolve the red precipitate and the mixture was filtered while hot to yield a red-violet solid. The solid was washed with MeOH and dried in air (1.362 g, 4.502 mmol).

Figure 40:
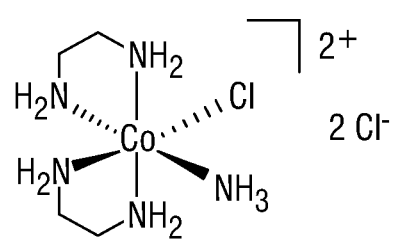
FIG. 40 shows the structure of cis-$[Co(en)2(NH_3)NO_3]Cl_2$ prepared by the procedure described in FIG. 38.

Referring to FIG. 40, cis-[Co(en)$_2$(NH$_3$)NO$_3$]Cl$_2$ was prepared. cis-[Co(en)$_2$(NH$_3$)Cl]Cl$_2$ (1.361 g, 4.502 mmol) was dissolved in H$_2$O (3 mL) and a solution of Hg(NO$_3$)$_2$ (2.55 g, 7.85 mmol) in concentrated HNO$_3$ (4 mL) was added. The solution stirred at room temperature for 30 min. during which time the color changed from violet to orange-red as a heavy white precipitate formed. The mixture was filtered though a plug of cotton and the filtrate was diluted with EtOH (100 mL). After a few minutes a sticky red precipitate formed. The flask was placed in an ice-bath and after 30 minutes the EtOH was decanted. A mixture of 1:1 EtOH/MeOH (100 mL) was added to the precipitate with vigorous stirring. After 5 minutes the alcohol solution was decanted and the red sticky residue was dried by oil pump vacuum at room temperature overnight to yield a flaky red solid that was hygroscopic when exposed to air (1.1854 g, 3.1016 mmol).

Figure 41:
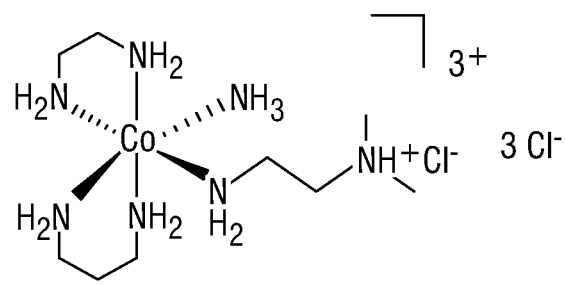
FIG. 41 shows the structure of cis-$[Co(en)_2(NH_3)\{(NH_2(CH_2)_2(NMe_2H+Cl—)\}]Cl_2$ prepared by the procedure described in FIG. 38.

Referring to FIG. 41, cis-[Co(en)$_2$(NH$_3$){(NH$_2$(CH$_2$)2 (NMe$_2$H+Cl—)}]Cl$_2$ was prepared. cis-[Co(en)$_2$(NH$_3$)NO$_3$] Cl$_2$ (1.1854 g, 3.1016 mmol) was dissolved in dry DMSO (5 mL) in a flame-dried Schlenk flask under N2 atmosphere. To the bright red solution was added N,N-dimethylethylenediamine (0.677 mL, 6.20 mmol). The solution was stirred at room temperature for 6 hours and a gradual color change from red to orange was observed and a small amount of white precipitate developed. The reaction mixture was filtered and the filtrate was diluted with H$_2$O (20 mL) and loaded onto a Dowex cation exchange column. The orange band that sorbed to the top of the column was washed with pure H$_2$O (100 mL) followed by 1 M HCl (100 mL). Then the band was eluted with 2 M HCl during which time a faint red band was separated from the intense orange band. The orange band was collected and concentrated by rotary evaporation to yield an orange hygroscopic solid (0.8688 g, 2.034 mmol). 13C NMR (DMSO-d6, 125 MHz) δ 56.6, 44.2, 44.0, 43.9, 43.3, 42.7, 42.5, 37.3.

EXAMPLE 14

Werner Complexes in Enantioselective Hydrogen Bond Mediated Catalysis

Despite being inexpensive and readily available in enantiopure form, Werner complexes of the type [Co(en)$_3$]$^{3+}$(en=ethylenediamine) ((+)-Λ-1/(−)-Δ-1), and related species, have had no applications in enantioselective organic synthesis since their first preparation nearly a century ago.[1] This derives from their poor solubility in organic solvents and the fact that the chelating amine ligands are non-labile, preventing metal based substrate activation. In light of recent advancements in asymmetric hydrogen bond mediated catalysis by chiral alcohols, amines, and thioureas,[2] it was conceived that the abundant nitrogen-hydrogen bonds incorporated in the ethylenediamine units could activate Lewis basic substrates towards nucleophilic addition. The enantiopure Δ-(−)-[Co(en)$_3$]$^3$±cation became soluble in CH$_2$Cl$_2$ solvent by pairing with the large, non-coordinating anion tetrakis[(3,5-trifluoromethyl)phenyl]borate (BAr$_f$-) and was used to catalyze the Michael addition of dimethyl malonate to trans-β-nitrostyrene in the presence of triethylamine base in 99% yield and 30% ee.

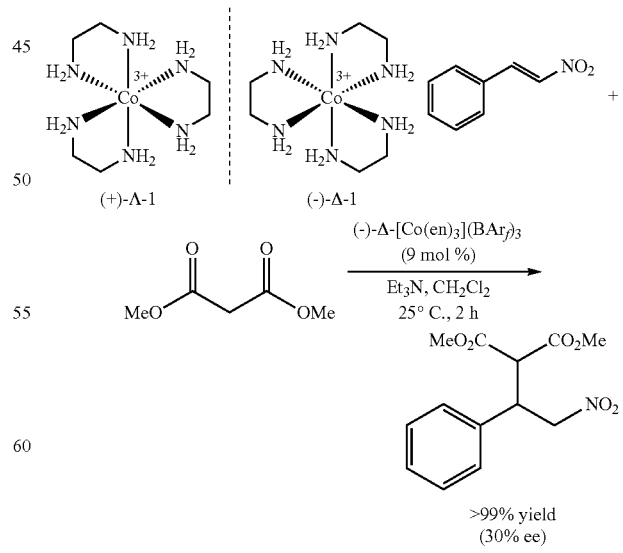

In efforts to improve enantioselectivity, related Werner-type complexes with bulky, enantiopure(1S,2S)-diphenylethylenediamine (S,S-dpen) ligands were synthesized. Thus, a diastereomeric mixture of (+)-Λ-[Co(S,S-dpen)₃]Cl₃ and (−)-(Δ)-[Co(S,S-dpen)₃]Cl₃ was prepared according to an earlier synthesis.[3] It was discovered that the anion exchange of these products with one molar equivalent of NaBAr$_f$ led to the CH₂Cl₂-soluble (+)-Λ-[Co(S,S-dpen)₃](BAr$_f$)Cl₂ ((+)-Λ-2) and (−)-(Δ)-[Co(S,S-dpen)₃](BAr$_f$)Cl₂ ((−)-Δ-2), which are easily separated by flash chromatography on silica gel.

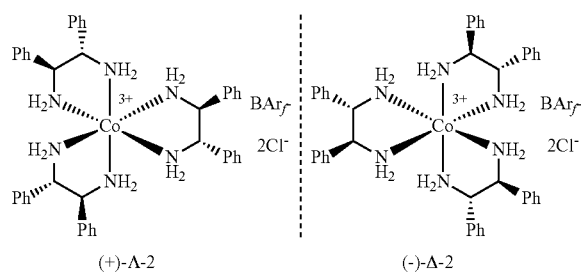

(+)-Λ-2        (−)-Δ-2

The Werner complex (+)-Λ-2 demonstrated marked improvement in the enantioselectivity of the Michael addition by catalyzing the reaction in 99% yield and 76% ee. Interestingly, the opposite catalyst diastereomer (−)-Δ-2, which bears the same absolute stereochemistry in the dpen ligand but the opposite sense of chirality at the metal center, promoted the same reaction with 99% yield and 56% ee of the opposite product enantiomer. This demonstrates that the enantioselectivity of the Michael addition is primarily under the control of the chirality at the metal center.

Some optimizations of the reaction conditions led to improved enantioselectivities. It is generally observed that weaker bases promote better selectivity. For instance, the use of pyridine gave the Michael addition product in 80% ee. Surprisingly, the catalyst system performed well even in polar solvents such as acetone, which promoted the Michael addition in 85% ee. This stands out as a unique feature, since most hydrogen bond mediating catalysts are strongly inhibited by polar solvents that are capable of competing with the substrate for hydrogen bonding sites. Additional examination reveals that enantioselectivity is even further improved in the presence of water and an inorganic base, giving up to 90% ee.

| Entry | Catalyst | Solvent | Base | % ee (% yield) |
|---|---|---|---|---|
| 1 | (−)-Δ-1 | CH₂Cl₂ | Et₃N | 30 S (99) |
| 2 | (+)-Λ-2 | CH₂Cl₂ | Et₃N | 76 R (99) |
| 3 | (−)-Δ-2 | CH₂Cl₂ | Et₃N | 56 S (99) |
| 4 | (+)-Λ-2 | CH₂Cl₂ | pyridine | 80 R (50) |
| 5 | (+)-Λ-2 | acetone | Et₃N | 85 R (99) |
| 6 | (+)-Λ-2 | CH₂Cl₂/H₂O | Na₂CO₃ | 90 R (99) |

The Michael addition of diphenylphosphite to trans-β-nitrostyrene was catalyzed by (+)-Λ-2 in 99% yield and 68% ee. The opposite catalyst diastereomer, (−)-Δ-2 promoted the same reaction in 99% yield to give the opposite product enantiomer in 72% ee, again emphasizing that the absolute product stereochemistry is determined by the chirality at the metal center.

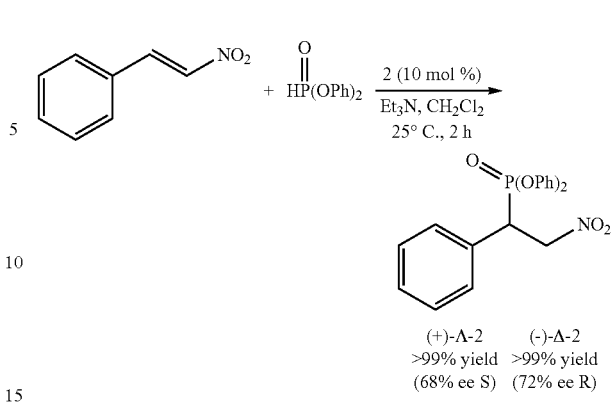

(+)-Λ-2    (−)-Δ-2
>99% yield   >99% yield
(68% ee S)   (72% ee R)

Several derivative Werner complexes have been synthesized with modified, enantiopure S,S-dpen ligands including complexes with electron donating (3), electron withdrawing (4), and sterically bulky functional groups (5).

3

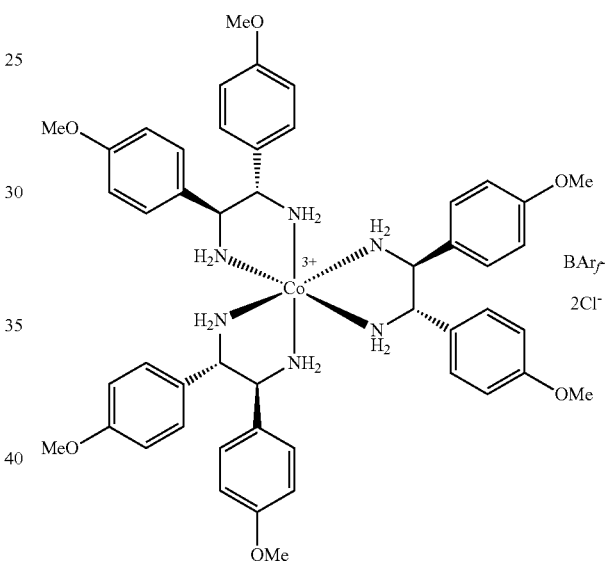

4

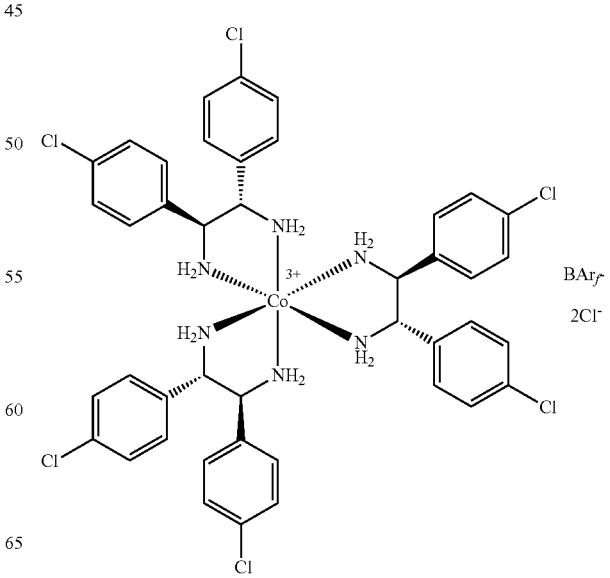

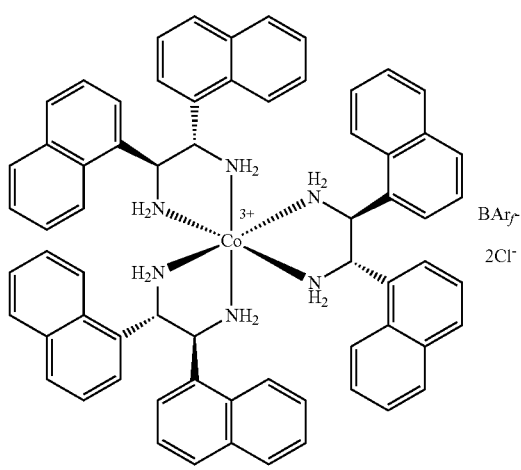

Werner-type complexes have here for the first time been successfully employed in enantioselective organic synthesis. The mode of activation by hydrogen bond mediation can be applied to a variety of substrates bearing hydrogen bond accepting functional groups. The structure of the S,S-dpen can be modified to allow for rapid fine tuning of the electronic and steric properties of the catalyst to suit a particular reaction. These Werner-type complexes are inexpensive to prepare owing largely to the low cost of cobalt and have been synthesized and resolved into pure diastereomers on a multi-gram scale. The catalysts are stable in the presence of air and moisture and are stored long term on the bench top. Lastly, recovery of the catalyst is possible by routine column chromatography during the purification of the reaction mixture.

References for Example 15
1) Werner, A. *Chem. Ber.* 1912, 45, 121.
2) Doyle, A. G.; Jacobsen, E. N. *Chem. Rev.* 2007, 107, 5713.
3) Bosnich, B.; Harrowfield, J. Mac. B. *J. Am. Chem. Soc.* 1972, 94, 3425.

The examples herein are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

REFERENCES

1. Ghosh, A. K.; Leshchenko-Yashchuk, S.; Anderson, D. D.; Baldridge, A.; Noetzel, M.; Miller, H. B.; Tie, Y. F.; Wang, Y.-F.; Koh, Y.; Weber, I. T.; Mitsuya, H. *J. Med. Chem.* 2009, 52, 3902.
2. Altman, J.; Ben-Ishai, D. *Tetrahedron: Asymmetry* 1993, 4, 91.
3. Ganzmann, C. Doctorate Thesis, Universität Erlangen-Nürnberg, 2010.
4. Chhabra, S. R.; Mahajan, A.; Chan, W. C. *J. Org. Chem.* 2002, 67, 4017.

What is claimed is:

1. A compound, comprising a transition metal complex having the formula $\Phi\text{-}[M\ ((x,y)\text{-}L_1)_{3-b-c}((w,v)\text{-}L_2)_b((t,u)\text{-}L_3)_c]^{p+}\text{An}^-_m, Z^-_{p-m}$, wherein $\Phi$ is $\Lambda$ or $\Delta$, wherein M is a transition metal, wherein p is an integer corresponding to the oxidation state of M, wherein each of x, y, w, v, t, and u independently comprises one of R and S, wherein each of $L_1$ and $L_2$ independently is a ligand comprising ethylene diamine, wherein $L_3$ is $EN(CH_2)_n NR_1 R_2$, wherein EN represents ethylene diamine, wherein n is from 2 to 4, and wherein $R_1$ and $R_2$ are independently H or alkyl groups, wherein c is from 1 to 3, wherein b is from 0 to 2, wherein $An^-$ comprises a lipophilic anion, wherein m is from 1 to 3, and wherein $Z^-$ comprises a second anion.

2. The transition metal complex according to claim 1, wherein the transition metal is selected from the group consisting of cobalt, iron, nickel, chromium, manganese, molybdenum, tungstsen, rhenium, ruthenium, technetium, osmium, rhodium, iridium, platinum, and palladium.

3. The transition metal complex according to claim 1, wherein the lipophilic anion is selected from the group consisting of tetrakis[(3,5-trifluromethyl)phenyl]borate), tetrakis[pentafluorophenyl]borate, carboranes of the general formula $CB_{11}H_{12}^-$, TRISPHAT of the general formula $P(O_2C_6Cl_4)_3^{3-}$, and 1,1'-Binaphthyl-2,2'-diyl phosphates.

4. The transition metal complex according to claim 1, wherein the transition metal complex has an enantioselectivity of at least 60% for one or more of a carbon-carbon bond forming reaction, a carbon-heteroatom bond forming reaction, and a carbon-hydrogen bond forming reaction.

5. The transition metal complex catalyst according to claim 1, wherein the transition metal complex has a conversion rate of at least 95% for the one or more of a carbon-carbon bond forming reaction, a carbon-heteroatom bond forming reaction, and a carbon-hydrogen bond forming reaction.

* * * * *